United States Patent
Dondio et al.

(12) 
(10) Patent No.: US 6,365,594 B1
(45) Date of Patent: *Apr. 2, 2002

(54) HETEROCYCLE-CONDENSED MORPHINOID DERIVATIVES (II)

(75) Inventors: Giulio Dondio, Garbagnate Mil.; Silvano Ronzoni, Seveso; Pier Andrea Gatti, S Genesio ed Uniti; Davide Graziani, Milan, all of (IT)

(73) Assignee: SmithKline Beecham S.p.A., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/101,213
(22) PCT Filed: Jan. 8, 1997
(86) PCT No.: PCT/EP97/00120
§ 371 Date: Feb. 22, 1999
§ 102(e) Date: Feb. 22, 1999
(87) PCT Pub. No.: WO99/25331
PCT Pub. Date: Jul. 17, 1997

(30) Foreign Application Priority Data

Jan. 10, 1996 (IT) .......................... MI96A0029
Nov. 5, 1996 (IT) .......................... MI96A2291

(51) Int. Cl.$^7$ .................... A61K 31/445; C07D 487/08; C07D 491/12; C07D 495/18
(52) U.S. Cl. .................. 514/279; 514/281; 514/282; 546/39; 546/40; 546/41; 546/43; 546/44; 546/45; 546/46; 546/47; 546/48; 546/49; 546/50; 546/56; 546/57
(58) Field of Search .................... 546/39, 40, 41, 546/43, 44, 45, 46, 47, 48, 49, 50, 56, 57; 514/279, 281, 282

(56) References Cited

U.S. PATENT DOCUMENTS

| 4,816,586 A | 3/1989 | Portoghese ................. 544/340 |
| 5,223,507 A | 6/1993 | Dappen et al. ............. 514/279 |
| 5,225,417 A | 7/1993 | Dappen et al. ............. 514/279 |
| 5,981,540 A | * 11/1999 | Dondio et al. ............. 514/279 |

FOREIGN PATENT DOCUMENTS

| EP | 0 456 833 | 6/1991 |
| EP | 0 614 898 | 4/1994 |
| GB | 2 175 898 | 5/1986 |
| WO | WO 96/02545 | * 2/1996 |

OTHER PUBLICATIONS

Schwarz et al., Heterocycles, 39(1), pp. 35–38 (1994).
Kotick et al., J. Med. Chem., 24(12), pp. 1445–1450 (1981).
Goerlitzer et al. (Parmazie (1992), 47(12), 893–7).*
Goerlitzer et al. (Parmazie (1992), 48(1), 30–33).*

* cited by examiner

*Primary Examiner*—Bruck Kifle
(74) *Attorney, Agent, or Firm*—Soma G. Simon; William T. King; Charles M. Kinzig

(57) ABSTRACT

Heterocycle-condensed morphinoid derivatives of formula (I), or solvates or salts thereof,

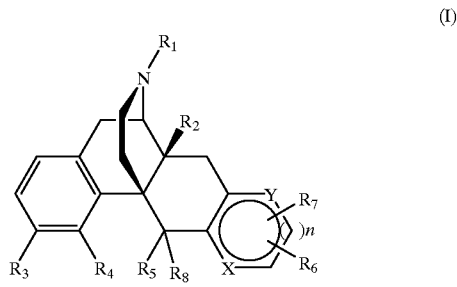

are potent and selective delta opioid agonists and antagonists and are useful as i.a. analgesics. Pharmaceutical compositions containing such compounds, the use of such compounds as therapeutic agents, a method of treatment comprising the administration of such compounds, and a process for the preparation of such compounds are also described.

7 Claims, No Drawings

HETEROCYCLE-CONDENSED MORPHINOID DERIVATIVES (II)

The present invention is concerned with novel morphinoid compounds, processes for their preparation and their use in medicine.

The presence of at least three populations of opioid receptors (mu, delta and kappa) is now well established and documented and all three appear to be present in the central and peripheral nervous system of many species including man (Lord J. A. H. et al., *Nature* 1977, 267, 495).

Activation of all three opioid receptor subtypes can lead to antinociception in animal models. In particular, studies with peptidic delta agonists have indicated that activation of the delta receptor produces antinociception in rodents, primates and can induce clinical analgesia in man (D. E. Moulin et al. *Pain,* 1985, 23, 213). Evidence exists that suggest a lesser propensity of delta agonists to cause the usual side-effects associated with mu and kappa activation (Galligan et al, *J. Pharm. Exp. Ther.,* 1984, 229, 641).

U.S. Pat. Nos. 5,223,507 and 5,225,417 (G. D. Searle & Co.) disclose bicycle-condensed morphinoid compounds which are said to be delta opioid agonists having therapeutic utility as analgesics agents.

WO 94/07896 (Toray Ind. Inc.) discloses indole-condensed morphinoid compounds useful as immunosuppressants, anti-allergic and anti-inflammatory agents.

We have now discovered a novel class of substituted monoheterocycle-condensed morphinoid derivatives which are potent and selective delta opioid agonists and antagonists which may therefore be of potential therapeutic utility as analgesics, immunosuppressants to prevent rejection in organ transplant and skin graft, anti-allergic and anti-inflammatory agents, brain cell protectant, agents for treating drug and alcohol abuse, gastritis, diarrhoea, cardiovascular and respiratory diseases, cough, mental illness and epilepsy and, in general, for the treatment of those pathological conditions which customarily can be treated with agonists and antagonists of the delta opioid receptor.

According to the present invention, there is provided a compound, or a solvate or salt thereof of formula (I):

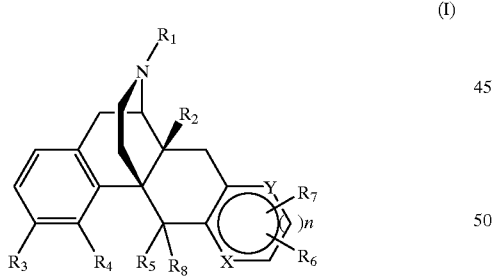

(I)

in which, $R_1$ is hydrogen, linear or branched $C_{1-6}$ alkyl, $C_{3-7}$ cycloalkyl, $C_{4-6}$ cycloalkylalkyl, each of the latter three groups being optionally substituted by a hydroxy group when $C_{\geq 2}$, $C_{3-5}$ alkenyl, aryl, aralkyl or furan-2 or 3-yl alkyl or $(CH_2)_mCOR$ wherein m is 0 to 5 and R represents linear or branched $C_{1-6}$ alkyl, hydroxy, $C_{1-5}$ alkoxy, $OC_{3-6}$ alkenyl or alkylaryl, $NR_{10}R_{11}$ where $R_{10}$ and $R_{11}$ may be the same or different, and each is hydrogen, linear or branched $C_{1-6}$ alkyl, $C_{4-6}$ cycloalkylalkyl, $C_{3-5}$ alkenyl, aryl or aralkyl; or $R_1$ is a group A-B wherein A represents $C_{1-10}$ alkylene and B represents substituted or unsubstituted aryl or heteroaryl;

$R_2$ is hydrogen, hydroxy or $C_{1-5}$ alkoxy, preferably methoxy, halogen, nitro, $NR_{10}R_{11}$, $SR_{10}$, where $R_{10}$ and $R_{11}$ have the same meaning described above and in addition $R_{10}$ is $COR_1$, preferably acetyl;

$R_3$ is hydrogen, linear or branched $C_{1-6}$ alkyl, preferably ethyl, hydroxy, $C_{1-5}$ alkoxy, preferably methoxy, halogen, preferably bromine, or $(CH_2)_mCOR$ where m and R have the same meaning described above, $SR_{10}$, nitro, $NR_{10}R_{11}$, $NHCOR_{10}$, $NHSO_2R_{10}$, where $R_{10}$ and $R_{11}$, have the same meaning described above, preferably hydrogen or methyl;

$R_4$ and $R_5$, which may be the same or different, are each independently hydrogen, hydroxy, $C_{1-5}$ alkoxy, preferably methoxy, O-phenyl or together may form an oxy group (—O—); or $R_4$ together with $R_3$ may form a methylendioxy group (—OCH2O—); $R_6$ is a group

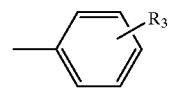

or a five- or six-membered heteroaromatic group, containing up to three heteroatoms such as O, S and N, substituted with $R_3$ in which $R_3$ has the same meaning described above, there being up to three $R_3$ groups in the ring, or $R_6$ is a group $C(Z)R_{12}$, in which Z is oxygen or sulphur, $R_{12}$ is linear or branched $C_{1-18}$ alkyl, hydroxy, linear or branched $C_{1-18}$ alkoxy, aralkyloxy or $NR_{13}R_{14}$, where $R_{13}$ and $R_{14}$, which may be the same or different, are hydrogen, linear or branched $C_{1-6}$ alkyl, $C_{3-7}$ cycloalkyl, $C_{4-6}$ cycloalkylalkyl, each of the latter three groups being optionally substituted by up to three fluorine atoms or hydroxy group when $C_{\geq 2}$, $C_{3-6}$ alkenyl, aryl, aralkyl or an optionally substituted heterocyclic ring or $R_{13}$ and $R_{14}$ may form together a $C_{3-6}$ alkyl ring which may be interrupted by an oxygen or a $NR_1$ where $R_1$ has the same meaning described above, or $R_6$ is a $CH_2WA$ group, where W is oxygen, sulphur or $NR_{14}$, and A is hydrogen, linear or branched alkyl or $COR_{14}$, where $R_{14}$ is defined above and is preferably methyl; or $R_6$ is a $COCOR_{12}$ group, where $R_{12}$ has the same meaning described above, and is preferably $C_{1-18}$ alkoxy;

or $R_6$ is a $NR_{13}R_{14}$ group, where $R_{13}$ and $R_{14}$ have the same meaning described above, or $R_{13}$ may be a $(CH2)mCOR$ group where m and R have the same meanings defined above;

or $R_6$ is a $P(Z)R_{12}$ group where Z and $R_{12}$ have the same meaning described above, and preferably Z=O and R12=$C_{1-18}$ alkoxy;

or $R_6$ is a $S(O)_iR_{12}$ group where i=1,2 and $R_{12}$ has the same meaning described above. $R_7$ is hydrogen, $C_{1-18}$ alkyl, $C_{2-18}$ alkenyl, halogen, halogen-$C_{1-6}$ alkyl, $(CH_2)_mCOR$ where m and R have the same meanings defined above or is a group

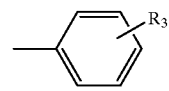

or a five- or six-membered heteroaromatic group, containing up to three heteroatoms such as O, S and N, substituted with $R_3$ in which $R_3$ has the same meaning described above, $R_8$ is hydrogen, $C_{1-6}$ alkyl preferably methyl;
n is 0 or 1;
when n=0, then X and Y are independently oxygen, sulphur, CH or a R6- or R7-substituted carbon atom, and $NR_9$, where $R_9$ is hydrogen, linear or branched $C_{1-6}$ alkyl, $C_{3-7}$ cycloalkyl, $C_{4-6}$ cycloalkylalkyl, each of the latter three groups being optionally substituted by a hydroxy group when $C_{\geq 2}$, or may contain a $NR_{10}R_{11}$ group where $R_{10}$ and $R_{11}$ have the same meaning described above, $C_{3-5}$ alkenyl, aryl, aralkyl or $(CH_2)_m COR$ wherein m is 0 to 5 and R represents hydroxy, $C_{1-5}$ alkoxy, $OC_{3-6}$ alkenyl or alkylaryl, $NR_{10}R_{11}$ where $R_{10}$ and $R_{11}$ may be the same or different, are each hydrogen, linear or branched $C_{1-6}$ alkyl, $C_{4-6}$ cycloalkylalkyl; and when n=1, then X and Y are both N, or N and CH.

When $R_1$ is aryl, it is preferably phenyl and when it is aralkyl, it is preferably phenyl-$C_{1-6}$ alkyl.

Examples of $R_1$ are hydrogen, methyl, ethyl, propyl, i-propyl, allyl, benzyl, phenyl-ethyl, $CH_2CH_2OH$, $CH_2COOH$, $CH_2COOEt$, $CH_2CONH_2$, and COMe.

Examples of $R_2$ are hydrogen, hydroxy and methoxy.

Examples of $R_3$ are hydrogen, hydroxy, ethyl, bromine, hydroxy, methoxy, ethoxy, i-propoxy, COMe and $OCH_2COOH$.

Examples of $R_4$ and $R_5$ are hydrogen, hydroxy, acetyloxy, methoxy, O-phenyl, together as an oxy group or $R_4$ together with $R_3$ is a methylendioxy group.

Examples of $R_6$ are $CONH_2$, $CONMe_2$, $CONEt_2$, CON(i-Pr)$_2$, CON(i-Pr)CH$_2$Ph, CON(i-Pr)(CH$_2$)$_2$OH, CON(CH$_2$CF$_3$)(i-Pr), COOMe, COOEt, COO-n-Pr, COO-i-Pr, and COO-i-Bu, COOCH(i-Pr)$_2$, CSNEt$_2$, CSN(i-Pr)$_2$, COOH, COMe, CO-i-Pr, CO-i-Bu, CO-t-Bu, CO-3-pentyl, COPh,

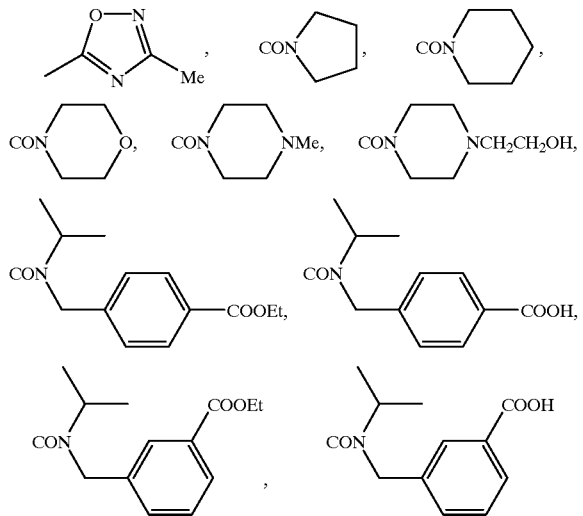

and PO(OEt)$_2$.

Examples of $R_7$ are methyl, i-propyl, trifluoromethyl, $CH_2COOH$ and $CH_2COOEt$.

An example of $R_8$ is hydrogen.

Examples of $R_9$ are hydrogen, methyl, $CH_2COOH$, $CH_2COOEt$, $CH_2CONHCH_2Ph$, $CH_2CONHMe$, $CH_2CONMe_2$.

Examples of X are $NR_9$, where $R_9$ are the same of the examples described above, and S.

Examples of Y are $CR_7$, where $R_7$ are the same of the examples described above.

A group of preferred compounds of formula (I) is that in which n=0, X is NH and Y is CH or a $R_6$- or $R_7$-substituted carbon atom, where $R_6$ is a group —C(Z)—$R_{12}$ where $R_{12}$ is $C_{1-6}$ alkyl, $C_{1-4}$ alkoxy or $NR_{13}R_{14}$ where $R_{13}$ and $R_{14}$ are as defined above and Z is oxygen; and $R_7$ is methyl or halogen-$C_{1-2}$alkyl.

Particularly preferred compounds of formula (I) are those in which $R_6$ is $CONEt_2$, CON(i-Pr)$_2$ or COO-i-Bu, $R_7$ is methyl, and $R_9$ is hydrogen, methyl or $CH_2COOH$.

The compounds of formula (I) or their salts or solvates are preferably in pharmaceutically acceptable or substantially pure form. By pharmaceutically acceptable pure form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (1) or its salt or solvate.

One preferred pharmaceutically acceptable form is the crystalline form, including such form in a pharmaceutical composition. In the case of salts and solvates the additional ionic and solvent moieties must also be non-toxic.

Examples of pharmaceutically acceptable salts of a compound of formula (I) include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

The compounds of formula (I) may exists in more than one stereoisomeric form, and the invention extends to all such forms as well as to their mixtures thereof, including racemates.

The invention also provides a process for the preparation of a compound of formula (I), or a solvate or salt thereof, which comprises condensing a compound of formula (a), where K is H, Br, $COR_7$, =CHOH or =NOH, with a compound of formula (b), where Q is $COR_7$, $CHClR_7$, $COR_7$, SH or $NH_2$, and J is =NNHPh, =O, =H$_2$, or =CHR, where $R_7$ and $R_6$ have the same meaning described above.

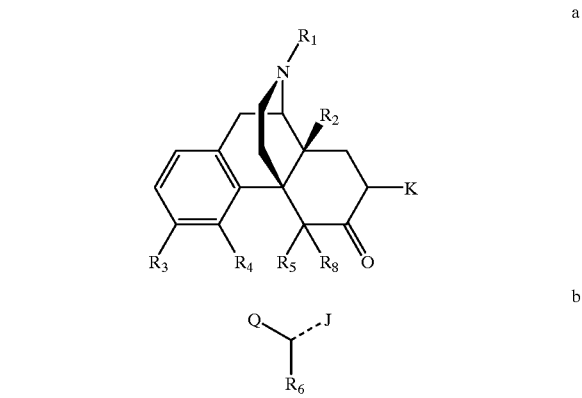

and optionally thereafter converting the compound of formula (I) to a solvate or salt thereof.

Preferred reaction conditions when K=H, Q=$COR_7$ and J==NNHPh are AcOH/Zn in presence of AcONa at the temperature in a range of 60–100° C.;

Preferred reaction conditions when K=$COR_7$, Q=SH and J==H$_2$ are i) dry HCl in alcoholic media at RT, ii) strong base e.g. MeONa in MeOH.

Preferred reaction conditions when K=H, Q=CHClR, and J==O are NaH in THF.

The compounds of formula (I), or salts or solvates thereof, may be prepared by the methods illustrated in the following general reaction schemes, or by modification thereof, using readily available starting materials, reagents and conventional synthetic procedures. If a particular enantiomer of a compound of the present invention is desired, it may be synthesised starting from the desired enantiomer of the starting material and performing reactions not involving racemization processes or it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxy, diastereomeric salts are formed with an appropriate optically active acid or base, followed by resolution of diastereomeric salts by fractional crystallization and subsequent recovery of the pure enantiomers.

Compounds (I) in which n=0, X=NH and Y is a $R_7$-substituted carbon atom, may be obtained starting from ketones of formula (II) and hydrazones of formula (III) (Organic Reactions, 1959, 3–142), in the presence of Zn and $CH_3COONa$ in $CH_3COOH$ as solvent (Khimiya Geterot. Soed., 1972, 342) as described in scheme 1:

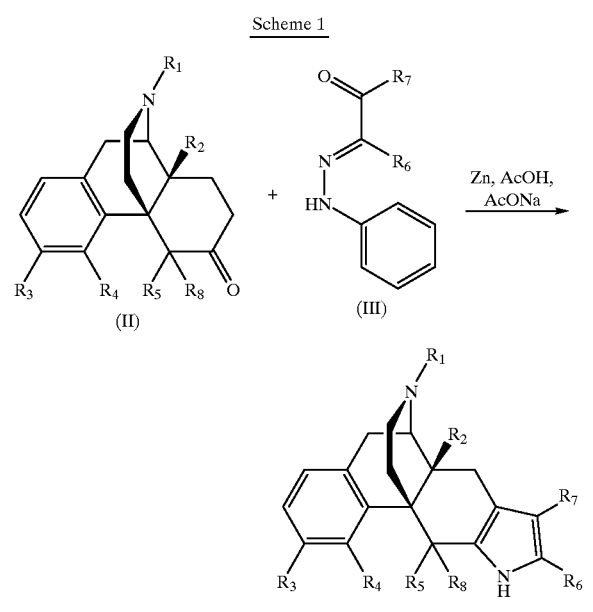

Compounds (1) in which n=0, X=NH and Y is a $R_6$-substituted carbon atom, may be obtained by cyclization of halogeno ketones of formula (IV) (J. Org. Chem, 1964, 29, 3459), with ketones of formula (V) in the presence of $NH_4OH$ (Can. J. Chem., 1970, 48, 1689) as described in scheme 2:

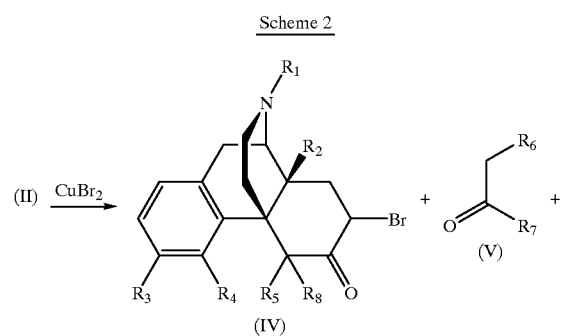

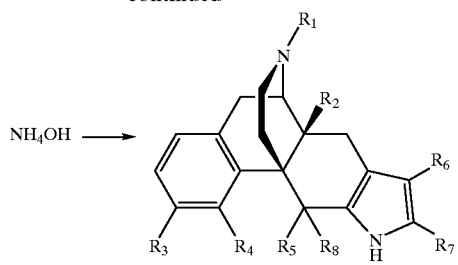

Compounds (I) in which n=0, X=O and Y is a $R_7$-substituted carbon atom, may be obtained by cyclising ketones of formula (II) with α-halogenoketones (preferably α-chloroketones) of formula (VI), in the presence of a base (J. Org. Chem., 1984, 49, 2317) as described in scheme 3:

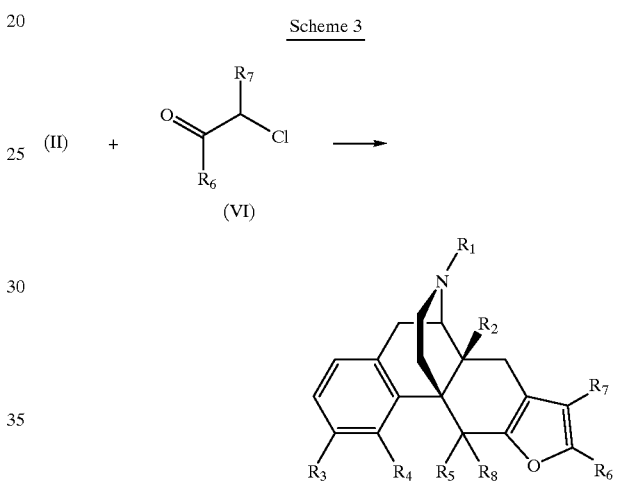

Compounds (I) in which n=0, X=O and Y is a $R_6$-substituted carbon atom, may be obtained by cyclization of the bromoketones (IV) with ketones (V) in ethanol in the presence of a base (preferably EtONa) (J. Chem. Soc. Perkin I, 1972, 2372) as described in scheme 4:

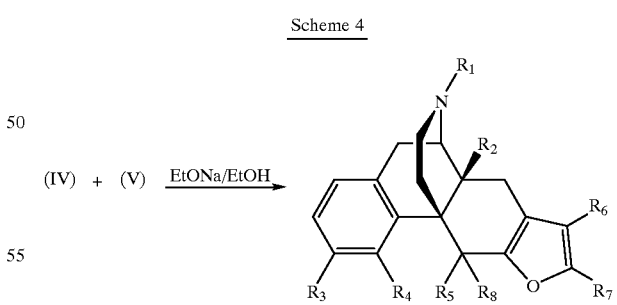

Compounds (I) in which n=0, X=S and Y is a $R_7$-substituted carbon atom, may be prepared from β-diketones of general formula (VII) (synthesised by Claisen reaction, starting from ketones (II) and esters of formula $R_7$-COOEt; J. Am. Chem. Soc., 1945, 67, 1510; J. Med. Chem. 1982, 25, 983) and mercapto derivatives of formula (VIII) in the presence of HCl (DE 1.088.507; C.A., 1962, 56, 456; Synthesis, 1992, 526) as described in scheme 5:

Scheme 5

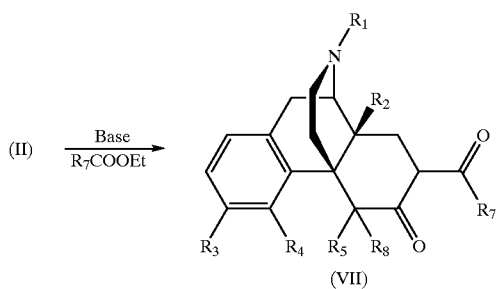

Scheme 7

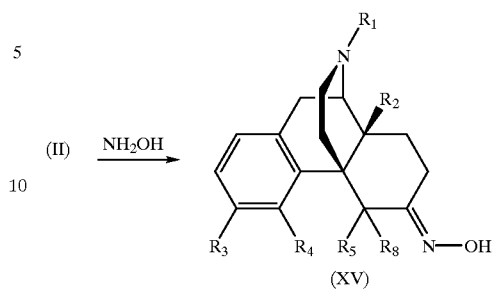

Compounds (I) in which n=0, Y=S and X is a $R_6$-substituted carbon atom, may be obtained by reacting α-mercaptoketones (IX) (which may be prepared starting from the bromoketones (IV) and $H_2S$/KOH, J. Am. Chem. Soc., 1985, 107, 4175) with an alkyne derivative of formula (X), in a solvent such as DMSO, in the presence of a base such as t-BuOK (Chem Ber., 1964, 97, 2109) as described in scheme 6:

Compounds (I) in which n=1, X=N and Y=CH may be obtained by reacting α-hydroxymethylenketones (XI) (which may be prepared from ketones (II) by condensation with HCOOEt in the presence of a base; Org. Synth. Coll., 1963, 4, 536) with enamines (XII) (J. Ind. Chem. Soc., 1935, 12, 289) as described in scheme 8:

Scheme 6

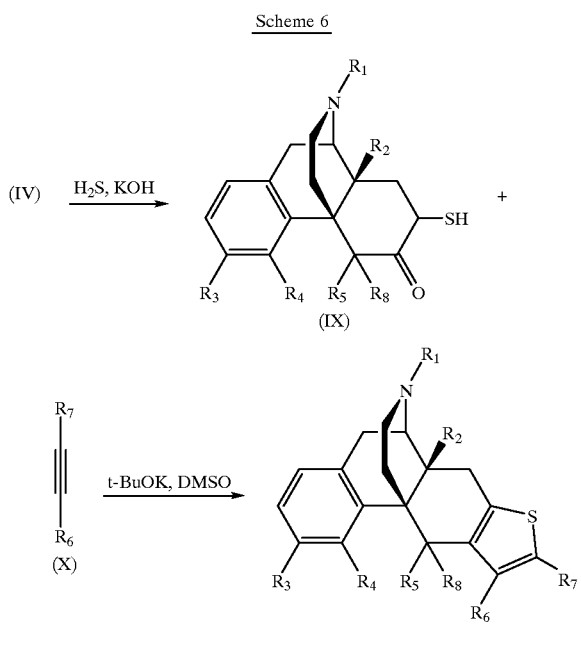

Scheme 8

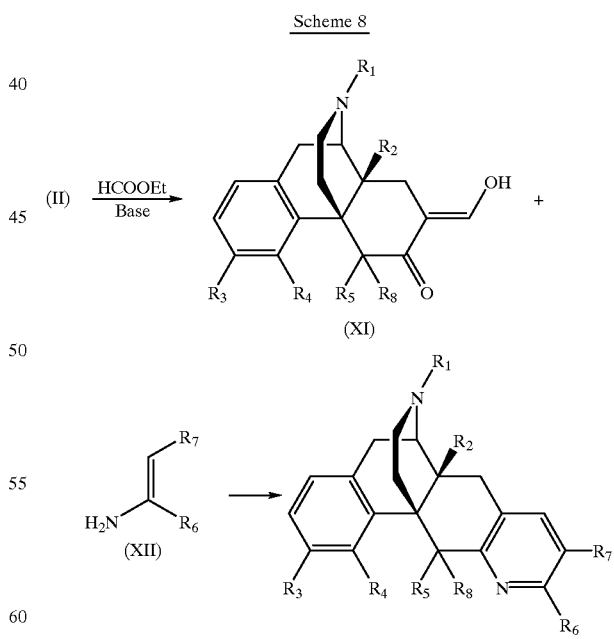

Compounds (I) in which n=0, X and Y are both N, may be obtained from hydroxyimino derivatives (XV) and $R_6$–$R_7$-substituted imidoyl chlorides of formula (XVI) in basic media, and subsequent treatment of the intermediates with H$^+$ in refluxing toluene (J. Org. Chem., 1993. 58, 7092) as described in the scheme 7:

Compound (I) in which n=1, and X=Y=N may be obtained starting from α-hydroxyiminoketones (XIII) (which may be prepared from ketones (II) and i-amylnitrite/t-BuOK as described in J. Med. Chem., 1991, 34, 1715) with ethanediamines (XIV) and subsequent aromatization of the interme diate in basic media (Chem. Ber., 1967, 100, 555) as described in scheme 9:

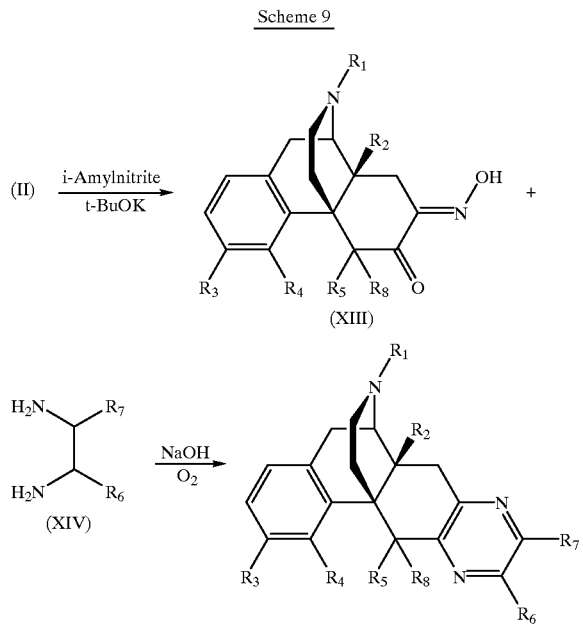

Compound of general formula (I') in which n=0, X=NH and Y is a $R_6$- or $R_7$-substituted carbon atom may be converted using an alkylating agent $R_9Br$ in the presence of NaH in DMF to obtain other compounds of general formula (I) in which the pyrrole nitrogen is substituted with a $R_9$ group as generally described in Scheme 10.

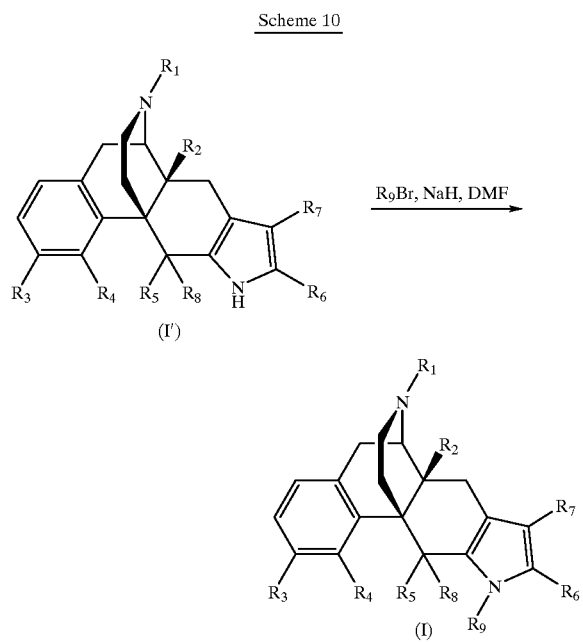

Compound of general formula (I') in which $R_4$=OH and $R_5$=H may be prepared from known ketones of formula (II) according to the Schemes described above or, alternatively, from compounds of general formula (I) in which $R_4$ and $R_5$ together form an oxy group (—O—), by reaction with Zn in boiling MeOH/HCl or boiling AcOH as described in the Scheme 11.

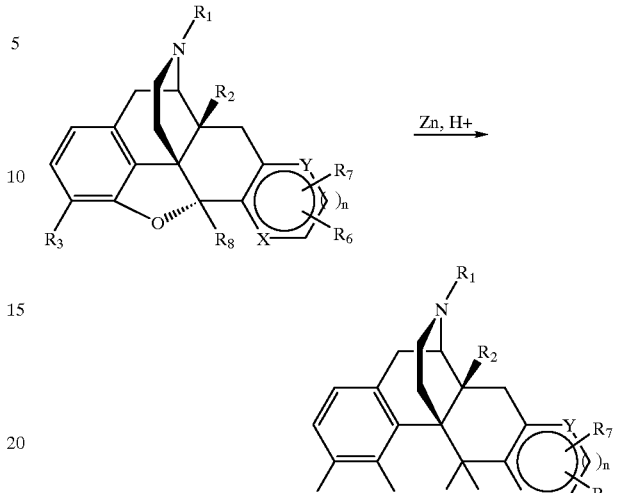

Compounds (I) in which n=0, X=S and Y=N, R6 is NR13R14 where R13 is (CH2)mCOR group where m=0 and R14 is hydrogen, may be obtained by cyclization of the bromoketones (IV) with thiourea in i-PrOH in the presence of a base (preferably Na2CO3) (J. Chem. Soc., 1945, 455) and subsequent acylation of the resulting amine with the appropriate acyl chloride or with the corresponding carboxylic acid in presence of a coupling reagent such as DCC as described in Scheme 12:

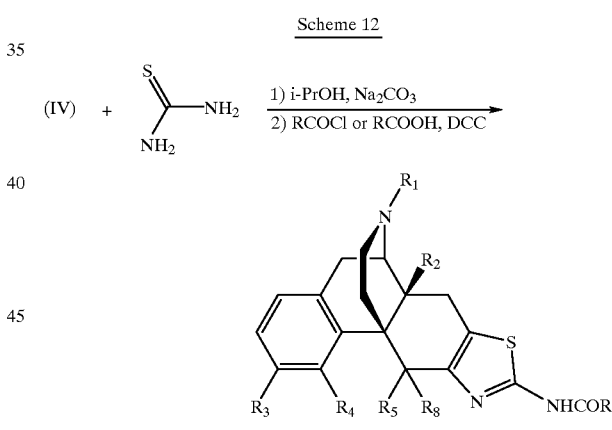

Compounds of general formula (I) in which $R_6$ ia a group $C(Z)R_{12}$, in which Z is sulphur may be prepared from compounds in which Z is oxygen by reaction with thiation agents such as Lawesson reagent.

Compounds of general formula (I) in which $R_6$=CH$_2$WA may be prepared from compounds of general formula (I) by conventional chemical reactions well known in literature of groups $R_6$ such as esters amides, tioamides.

The compounds of formula (I) may be converted into their pharmaceutically acceptable salts by reaction with the appropriate organic or mineral acids.

Solvates of the compounds of formula (I) may be formed by crystallization or recrystallization from the appropriate solvent. For example, hydrates may be formed by crystallization or recrystallization from aqueous solutions, or solutions in organic solvents containing water.

Also salts or solvates of the compounds of formula (I) which are not pharmaceutically acceptable may be useful as intermediates in the production of pharmaceutically acceptable salts or solvates. Accordingly such salts or solvates also form part of this invention.

In general compounds of formula (I) acting as selective delta receptor ligands may be useful as analgesics, immunosuppressants to prevent rejection in organ transplant and skin graft, anti-allergic and anti-inflammatory agents, brain cell protectant, for the treatment of drug and alcohol abuse, to decrease gastric secretion, for the treatment of diarrhoea, cardiovascular and respiratory diseases, cough and respiratory depression, mental illness, epileptic seizures and other neurologic disorders (herein after referred to as 'Conditions'). In particular, the activity of the compounds of formula (I) as delta agonists in standard tests indicates that they are of potential therapeutic utility as analgesic agents for the amelioration or elimination of pain.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of the Conditions.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known agents for treating the Conditions.

Preferably, a pharmaceutical composition of the invention is in unit dosage form and in a form adapted for use in the medical or veterinarial fields. For example, such preparations may be in a pack form accompanied by written or printed instructions for use as an agent in the treatment of the Conditions.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fibers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcerlulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

The compounds of this invention may also be administered by inhalation, via the nasal or oral routes. Such administration can be carried out with a spray formulation comprising a compound of the invention and a suitable carrier, optionally suspended in, for example, a hydrocarbon propellant Preferred spray formulations comprise micronised compound particles in combination with a surfactant, solvent or a dispersing agent to prevent the sedimentation of suspended particles. Preferably, the compound particle size is from about 2 to 10 microns.

A further mode of administration of the compounds of the invention comprises transdermal delivery utilising a skin-patch formulation. A preferred formulation comprises a compound of the invention dispersed in a pressure sensitive adhesive which adheres to the skin, thereby permitting the compound to diffuse from the adhesive through the skin for delivery to the patient. For a constant rate of percutaneous absorption, pressure sensitive adhesives known in the art such as natural rubber or silicone can be used.

As mentioned above, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

No unacceptable toxicological effects are expected with compounds of the invention when administered in accordance with the invention.

The present invention also provides a method for the treatment and/or prophylaxis of the Conditions in mammals, particularly humans, which comprises administering to the mammal in need of such treatment and/or prophylaxis an effective amount of a compound of formula (I) or a pharmaceutically acceptable salt or solvate thereof.

The activity of the compounds of the present invention as selective delta ligands is determined in radioligand binding assays as described below.

Mouse brain membranes were prepared as described by Kosterlitz (*Br. J. Pharmacol.*, 1981, 73, 939.). The binding of the preferential delta ligand [$^3$H]-[D-Ala$^2$,D-Leu$^5$]-enkephalin (DADLE) was evaluated at its $K_D$ concentration (1.3 nM) in presence of 40 nM of the unlabelled mu ligand [D-Ala$^2$, MePhe$^4$, Gly-ol$^5$]-enkephalin (DAMGO). The binding of the mu ligand [$^3$H]-DAMGO (*Eur. J. Pharmacol.*, 1989, 166, 213) and of the kappa ligand [$^3$H]-U69593 (*Excerpta Medica*, 1990, 211) were carried out at 0.5 nM. The non-specific binding was determined in presence of naloxone (10 $\mu$M) for all tritiated ligands. Binding data were expressed as percentage of inhibition and fitted the following equation: $f(x)=100 \cdot X/(IC_{50}+X)$ where X are cold drug concentration values. The $IC_{50}$ obtained were used to calculate the inhibitory constants ($K_i$) accordingly to the Cheng and Prusoff relation (*Biochem. Pharmacol.*, 1973, 22, 3099).

The delta agonist/antagonist activity of the compounds of the present invention is determined in the cAMP bioassay in NG108-15 cell lines as described below.

NG 108-15 cell were grown at 37° C. in humidified atmosphere of 5% $CO_2$ and 95% air in DMEM (without sodium pyruvate using 4500 mg/l glucose) supplemented with 10% foetal calf serum containing 2 mM glutamine, 2% HAT×50 supplement, 50 $\mu$g streptomycin and 50 I.U. penicillin per ml confluent cells were harvested with 1M EDTA in Ca/Mg-free phosphate-buffered saline with mechanical stiring. Medium was replaced every 2 day. One day before the experiment the cells were dispensed in 17 mm culture plate (about 10×10$^6$ cells/plate). After 1 day, the growth medium was removed and cells washed twice with a modified Krebs-Ringer medium buffered with hepes-NaOH 200 mM, pH 7.4, that contained (mmol/l): NaCl (125), KCl (5), $KH_2PO_4$ (0.4), $MgSO_4$ and $CaCl_2$ (1.2) $NaHCO_3$ (25), glucose (12). Incubation medium was also including 1 mM 3-isobuthyl-1-methylxantine (IBMX). Experiments were performed at room temperature. After incubation for 10 minutes to allow IBMX incorporation, NG108-15 cells were exposed to 1 $\mu$M forskolin and the compound to be tested, for 10 minutes. The reaction was terminated by adding cold 0.4N $HClO_4$. After 15 minutes, the cold surnatants were carefully collected and neutralised using 1M $KC_2O_3$. After an overnight incubation at 4° C. the tubes were centrifuged at 9000 rpm for 5 minutes and a 100 $\mu$l aliquot tested for cAMP content by using the commercially available $^{125}$I cAMP RIA kit (Amersham Inc.). The pellets from the original plates were dissolved in NaOH 0.5N and the protein content was determined with the method described by Bradfort (*Anal. Biochem.* 1976, 72, 248). The data were normalised to protein content.

The most potent compounds described in the present invention showed affinities for the delta receptor ranging from 0.5 to 200 nM with delta selectivity ranging from 20 to 1500 times in respect to the other opioid receptor types. These compounds displayed also potent delta agonist or antagonist properties in the cAMP inhibition bioassay. Selective delta agonists (antagonised by the selective delta antagonist naltrindole) displayed $IC_{50}$s ranging from 1 to 500 nM. For example, the compound of Example 10 shows a Ki delta=2.9 nM, Ki mu/Ki delta=840 and Ki kappa/Ki delta=600. The compound of Example 1 showed an agonist activity in the inhibition of forskolin-stimulated cAMP in NG108-15 cells ($IC_{50}$=15 nM) completely antagonised by the selective delta antagonist naltrindole (100 nM).

Mouse abdominal constriction (MAC) (*Proc. Soc. Exp. Biol. Men*, 1957, 95, 729), mouse tail-flick (MTF) (*J. Pharm. Exp. Ther.*, 1941, 72, 74) and mouse tail-flick warm water (MTF-WW) (*Life Sci.*, 1986, 32, 1795) were adopted to evaluate the antinociceptive efficacy of the compounds of the present invention.

The following preparations 1 to 7 illustrate the synthetic procedure to obtain new ketones of general formula (II) that, as such, form a part of the present invention. In particular 4,5-epoxy-17-methyl-3-vinylmorphinan-6-one, 4,5-epoxy-3-(1-ethoxyvinyl)-17-methylmorphinan-6-one, 4,5-epoxy-3-ethyl-17-methylmorphinan-6-one, 3-bromo-4,5-epoxy-14-hydroxy-17-methylmorphinan-6-one and 3-bromo-4,5-epoxy-17-methylmorphinan-6-one are novel compounds and are utilised as starting materials to prepare the compounds of Examples 28, 30, 33, 35, 41, 52, 61 and 64. Other ketones used as starting materials are known in the literature. Preparation 8 illustrates the preparation of a new phosphonohydrazone of general formula (III) that was used as starting material to prepare the compound of Example 89. Example 1 illustrates the preparation of compounds of general formula (I) of the present invention starting from the corresponding ketones of general formula (II) and the corresponding known hydrazones of general formula (III). Examples 2, 49 and 52 illustrate the preparation of compounds of general formula (I) which are in turn prepared by chemical transformation of the corresponding compounds of formula (I). Example 105 describes the preparation of compounds of general formula (I) in which n=0, X=S and Y is a substituted carbon atom. The Examples described herein are prepared according to the same procedures as described for Examples 1, 2, 49, 52 and 105.

The compounds of the Examples 1 to 105 are summarised in the Chemical Table.

General procedure for the preparation of compounds of general formula (II) in which $R_3$=CH=CH$_2$ and C(OEt)=CH$_2$.

Preparation 1

4,5-Epoxy-17-methyl-3-trifluoromethanesulfonyloxymorphinan-6-one 5.5 g (19.3 mmol) of 4,5-epoxy-3-hydroxy17-methylmorphinan-6-one were dissolved in 20 ml of pyridine under a nitrogen atmosphere. The solution was cooled to 0° C. and 3.56 ml (21.2 mmol) of trifluoromethanesulfonic anhydride were added dropwise. The solution was stirred for 5 min at 0° C. and then allowed to warm to room temperature overnight. The reaction mixture was poured onto water and the aqueous phase was extracted with AcOEt. The organic phase was dried over $NA_2SO_4$ and the solvent removed in vacuo. The crude reaction mixture was purified by flash chromatography, eluting with a mixture $CH_2Cl_2$/MeOH/conc. $NH_4OH$ 90:7:0.7 respectively, yielding 6.26 g of the title product.

N.M.R. 300 MHz ($CDCl_3$): δ7.0 (d, 1H), 6.7 (d, 1H), 4.7 (s, 1H), 3.2 (m, 1H), 3.1 (d, 1H), 2.7–2.3 (m, 8H), 2.1 (m, 2H), 1.9–1.7 (m, 2H), 1.3–1.1 (m, 1H).

MS (TSP) m/z=417.2 ($M^+$)

Preparation 2

4,5-Epoxy-17-methyl-3-vinylmorphinan-6-one 2 g (4.8 mmol) of 4,5-epoxy-17-methyl-3-trifluoromethanesulfonyloxymorphinan-6-one were dissolved, under a nitrogen atmosphere, in 25 ml of dimethylformamide, then 1.46 ml (5 mmol) of vinyltributyltin, 1.6 g (38.4 mmol) of LiCl, 0.337 g (0.48 mmol) of bis(triphenylphosphine)palladium(II) chloride and 0.5 g (1.9 mmol) of triphenylphosphine were added. The reaction mixture was heated to 100° C. for 3 h, then it was poured onto water and the aqueous phase was extracted with AcOEt. The organic phase was dried over $Na_2SO_4$ and the solvent was removed in vacuo. The crude reaction mixture was purified by flash chromatography, eluting with a mixture $CH_2Cl_2$/MeOH/conc. $NH_4OH$ 90:7:0.7 respectively, yielding 1.1 g of the title product.

N.M.R. 300 MHz ($CDCl_3$): δ7.1 (d, 1H), 6.8–6.6 (m, 2H), 6.0 (d, 1H), 5.4 (d, 1H), 4.6 (s, 1H), 3.2–1.7 (m, 13H), 1.2 (m, 2H).

MS (TSP) m/z=295.1 ($M^+$)

Preparation 3

4,5-Epoxy-3-(1-ethoxyvinyl)-17-methylmorphinan-6-one 2.5 g (6.0 mmol) of 4,5-epoxy-17-methyl-3-trifluoromethanesulfonyloxymorphinan-6-one, 2.1 ml (6.2 mmol) of (1-ethoxyvinyl)tributyltin, 2 g (48 mmol) of LiCl, 0.42 g (0.6 mmol) of bis(triphenylphosphine)palladium(II) chloride and 0.63 g (2.4 mmol) of triphenylphosphine in 25 ml of dimethylformamide were treated as described in Preparation 2. The crude reaction mixture was purified by flash chromatography, eluting with a mixture $CH_2Cl_2$/MeOH/conc. $NH_4OH$ 90:7:0.7 respectively, yielding 1.95 g of the title product.

I.R. (KBr): 2932, 1728, 1674 $cm^{-1}$.

N.M.R. 300 MHz ($CDCl_3$): δ7.4 (d, 1H), 6.6 (d, 1H), 5.2 (s, 1H), 4.65 (s, 1H), 4.45 (s, 1H), 3.9 (q, 2H), 3.2–1.4 (m, 18H).

MS (TSP) m/z=339.1 ($M^+$).

Preparation 4

4,5-Epoxy-3-ethyl-17-methylmorphinan-6-one 1.2 g (4.06 mmol) of 4,5-epoxy-17-methyl-3-vinylmorphinan-6-one were dissolved in 150 ml of absolute EtOH. 1 g of 10% Pd on charcoal was added and the reaction mixture was hydrogenated in a Parr apparatus at 35 psi and at room temperature for 8 h. The catalyst was filtered off and the solvent was removed in vacuo, yielding 0.77 g of the title product.

N.M.R. 300 MHz ($CDCl_3$): δ6.9 (d, 1H), 6.6 (d, 1H), 4.6 (s, 1H), 3.2–1.7 (m, 18H), 0.9 (m, 2H).

MS (TSP) m/z=297.1 ($M^+$)

General procedure for the preparation of compounds of general formula (II) in which $R_3$=Br Preparation 5

3-Bromo4,5-epoxy-17-methylmorphinan-6-ol 3.1 g (11.4 mmol) of 4,5-epoxy-17-methylmorphinan-6-ol were dissolved in 150 ml of glacial acetic acid and 11.4 ml of a 1M solution of $Br_2$ in AcOH were added dropwise. After 1 h, AcOH was removed in vacuo, the residue was taken up with water, the aqueous solution was brought to pH 7 with a saturated $NAHCO_3$ solution and extracted with AcOEt. The organic phase was dried over $NA_2SO_4$, the solvent was removed in vacuo, yielding 3.6 g of the title product.

I.R. (KBr): 3580, 2930, 1452 $cm^{-1}$.

N.M.R. 300 MHz ($CDCl_3$): δ7.2 (d, 1H), 6.6 (d, 1H), 4.6 (d, 1H), 4.0 (m, 1H), 3.1 (m, 1H), 2.9 (d, 1H), 2.5–1.5 (m, 12H), 1.1 (m, 1H).

MS (TSP) m/z=349.0 (M-1)

Preparation 6

3-Bromo-4,5-epoxy-14-hydroxy-17-methylmorphinan-6-one 1.1 g (3.8 mmol) of 4,5-epoxy-14-hydroxy-17-methylmorphinan-6-one in 50 ml of glacial AcOH were treated with 3.8 ml of a 1M solution of $Br_2$ in AcOH as described in Preparation 5, yielding 1.1 g of the title product.

I.R. (KBr): 3348, 2910, 1738 $cm^{-1}$.

Preparation 7

3-Bromo-4,5-epoxy-17-methylmorphinan-6-one

A solution of 1.6 ml of DMSO in 4.8 ml of $CH_2Cl_2$ was added slowly, under a nitrogen atmosphere and at -55° C., to a solution of 0.9 ml of oxalyl chloride in 21 ml of $CH_2Cl_2$. After 2 min. 3.6 g (10.3 mmol) of 3-bromo-4,5-epoxy-17-methylmorphinan-6-ol in 20 ml of $CH_2Cl_2$ were added, followed, after 15 min. by 6.6 ml of $Et_3N$. The reaction mixture was allowed to warm up to room temperature in 2 h, then it was quenched with 50 ml of $H_2O$. The phases were separated, the organic phase was dried over $NA_2SO_4$ and the solvent was removed in vacuo. The crude reaction mixture was purified by flash chromatography, eluting with a mixture $CH_2Cl_2$/MeOH/conc. $NH_4OH$ 90:7:0.7 respectively, yielding 2.87 g of the title product.

I.R. (KBr): 2940, 1716, 1446 $cm^{-1}$.

N.M.R. 300 MHz ($CDCl_3$): δ7.2 (d, 1H), 6.6 (d, 1H), 5.4 (s, 1H), 3.3 (m, 1H), 2.95 (d, 1H), 2.6–1.7 (m, 12H), 1.2 (m, 1H).

MS (TSP) m/z=347.0 (M-1)

Preparation 8

Diethyl-1-phenylhydrazono-2-oxopropylphosphonate

To a solution of 5.0 g (0.0257 mol) of diethyl(2-oxopropyl)phosphonate in 25 ml of ethanol/water 4:1, were added 7.1 g (0.0517 mol) of $K_2CO_3$ and 0.0257 mol of phenyldiazonium chloride at 10° C. The resulting suspension was stirred until the temperature reached the room temperature. Then 30 ml of water and ml 100 of $CH_2Cl_2$ were added. The organic layer was dried on $Na_2SO_4$ and evaporated in vacuo yielding 7 g of the title compound as red oil which was used as such in the subsequent step. $C_{13}H_{19}N_2O_4P$ IR (neat): 3498, 1716, 1666, 1268, 1026 $cm^{-1}$.

N.M.R. 300 MHz (CDCl$_3$): δ12.9 (bs, 1H); 7.5–7.0 (m, SH), 4.2 (m, 4H); 2.3 (s, 3H); 1.5 (m, 6H).

EXAMPLE 1

[R-(4bS*,8α,s8aβp,12βp)]11(N-N-benzylN-isopropylaminocarbonyl)-7,10dimethyl-1-methoxy-5,6,7,8,12,12b-hexahydro-(9H){4,8methanobenzofuro[3,2]pyrrolo[2,3-g]soquinoline hydrochloride 0.65 g (2.17 mmoles) of 7,8-dihydrocodeinone hydrochloride, 2.2 g (6.51 mmoles) di N-benzyl-N-isopropyl-2-phenylhydrazone-3-oxobutkamide, were dissolved in a mixture of 10 ml di glacial acetic acid and 0.54 g (6.51 mmoles) of CH$_3$COONa The resulting reaction mixture was warmed to 60° C., then 0.57 g (8.6 mmoles) of Zn dust were added portionwise and under nitrogen atmosphere. The mixture was refluxed for 2 h, and then cooled to room temperature. The resulting salts were eliminated by decantation and washed with acetic acid. The acidic solutions were collected and then brought to pH 8 and extracted several times with AcOEt. The organic phase was dried and evaporated to dryness in vacuo. The resulting residue was purified by medium pressure chromatography using silica gel (15–25 ) and a mixture of AcOEt/MeOH/NH4OH conc. 90:10:0.5 as eluenL The product was taken up in a mixture of acetone tMeOH 1:1 and the solution was brought to acidic pH with HCl/Et$_2$O. The resulting precipitate was filtered, washed and dried yielding 0.5 g of the title compound. M.P.=304° C. dec.

EXAMPLE 2

[8R-(4bS*,8α,8aβ,12bβ)]-11-Diethylaminothiocarbonyl-7,10-dimethyl-1-methoxy-5,6,7,8,12,12b-hexahydro-(9H)-4,8-methanobenzofuro[3,2-e]pyrrolo[2,3-g]isoquinoline hydrochloride 1 g (2.3 mmoles) of [8R-(4bS*,8α,8aβ,12bβ)]-11-diethylaminocarbonyl-7,10-dimethyl-1-methoxy-5,6,7,8,12,12b-hexahydro-(9H)-4,8-methanobenzofuro[3,2-e]pyrrolo[2,3-g]isoquinoline, 0.950 g (2.3 mmoles) of the Lawesson reagent, were dissolved in 40 ml of toulene and the mixture refluxed for 4 h. The solvent was removed in vacuo, then the residue was taken up in CH$_2$Cl$_2$ and washed with s.s. NaHCO$_3$. The organic layer was dried on Na$_2$SO$_4$. After evaporation of the solvent, the residue was purified with flash chromatography on silica gel (CH$_2$Cl$_2$/MeOH/NH$_4$OH conc. 86:10:0.6) then the product was dissolved in acetone. The resulting solution was brought to acidic pH with HCl/Et$_2$O. The precipitate was filtered, dissolved in boiling MeOH in presence of charcoal for 30'. The charcoal was filtered off, and the solution was evaporated to dryness. The residue was triturated. with boiling Et$_2$O yielding 0.41 g of the title compound. M.P.>250° C.

The compound of Example 73 was prepared according to the same procedure described above.

EXAMPLE 49

[8R-(4bS*,8α,8aβ,12b,β)]-11-Isopropylcarbonyl-7,10,12-trimethyl-1-methoxy-5,6,7,8,12,12b-hexahydro-[9H]-4,8-methanobenzofuro[3,2e]pyrrolo[2,3-g]isoquinoline hydrochloride 0.52 g (1.2 mmoles) of [8R-(4bS*,8α,8aβ,12bβ)]-11-isopropylcarbonyl-7,10-dimethyl-1-methoxy-5,6,7,8,12,12b-hexahydro-[9H]-4,8-methanobenzofuro[3,2-e]pyrrolo[2,3-g]isoquinoline (Example 34) were dissolved in 5 ml of DMF under nitrogen atmosphere. 0.051 g of 60% NaH was added portionwise maintaining the temperature of 0° C. After 30' a solution of 0.2 g of MeI dissolved in 1 ml of DMF was added dropwise. The reaction was quenched after 1 h with using crushed ice. The resulting solution was exhaustively with Et$_2$O. The organic layers were dried over Na$_2$SO$_4$ and then the solvent in vacuo. The resulting residue was dissolved in acetone and the solution brought to acidic pH with Et$_2$O/HCl. The solvent was in turn evaporated and the resulting residue was triturated with boiling Et$_2$O. The solid was filtered, washed and dried to yield 0.25 g of the title compound. M.P. 240–243° C.

The compounds of Examples 62 and 82 were prepared according to the procedure described above.

The compounds of Examples 74, 79 and 80 were prepared following the same procedure using as alkylating agent ethylbromoacetate. The resulting ethylesters were in turn hydrolysed in acidic conditions to the corresponding acid derivatives of the above Examples.

EXAMPLE 52

[10R, 4bS-(4bb, 9ab)]-3-Bromo-7-diisopropylaminocarbonyl-8,14-dimethyl-4b,5,9,9a,10,11-hexahydro-4-hydroxy-(6H)-10,4b-(iminoethano)phenanthro[3,2-b]pyrrole 0.3 g (0.58 mmol) of [8R-(4bS*,8a,8ab,12bb)]-1-bromo-11-diisopropylamino carbonyl-7,10-dimethyl-5,6,7,8,12,12b-hexahydro-(9H)-4,8-methanobenzofuro[3,2-e]pyrrolo[2,3-g]isoquinoline (Example 30) were dissolved, under a nitrogen atmosphere, in 10 ml of glacial AcOH and 0.15 g (1.8 mmol) of AcONa were added. The reaction mixture was heated to 80° C. and 0.23 g (3.5 mmol) of Zn dust were added portionwise. The reaction mixture was heated to reflux for 4 h, then it was poured onto ice, the pH was adjusted to 9 with conc. NH4OH and it was extracted with CH2Cl2. The organic phase was dried over Na2SO4 and the solvent was removed in vacuo. The crude reaction mixture was purified by flash chromatography, eluting with a mixture CH2Cl2/MeOH/conc. NH4OH 90:7:0.7 respectively. The resulting solid was triturated in Et2O, yielding 0.15 g of the title product.

EXAMPLE 105

[8R-(4bS*,8α,8aβ,12bβ)]-11-Methoxycarbonyl-7,10-dimethyl-1-methoxy-5,6,7,8,9,12b-hexahydro-4,8-methanobenzofuro [3,2-e]thieno[2,3-g]isoquinoline hydrochloride A solution of 7-acetyl-4,5-epoxy-1-methoxy-17-methylmorphinan-6-one (1 g, 2.9 mmol.) (J. Med. Chem. 1982, 25, 983) in MeOH (40 mL) was cooled at −10° C. and a stream of dry HCl was bubbled into the system until saturation (~1 h.). Then, thioglycolic acid (0.4 mL, 5.8 mmol) was added, and the bubbling of HCl was continued at −10° C. for 4 h. The mixture was left at RT for 6 days. The solvent was evaporated in vacuo, the residue treated with conc. NH$_4$OH and extracted with AcOEt. The organic layer was separated, washed with water, dried (Na$_2$SO$_4$) and evaporated in vacuo. The crude product was directly used in the next step.

A 2N solution of MeONa (10 ml) was added to a solution of the above product in 12 ml MeOH was added and kept under nitrogen for 24 h. The solvent was evaporated and the residue treated with ice-cold water. The mixture was acidified with 6N HCl to pH=1. After washing with AcOEt the aqueous layer was treated with NaOH to pH=9 and extracted with AcOEt. The solvent was dried, evaporated and the crude product was purified by silica gel chromatography ($CH_2Cl_2$/MeOH/conc. $NH_4OH$; 95:5:0.5). The resulting product was treated with HCl/$Et_2O$ yielding 55 mg of the title compound.

CHEMICAL TABLE

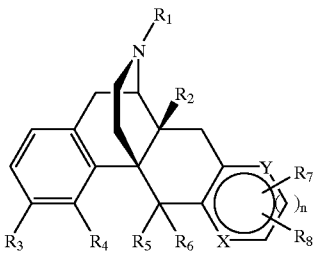

| Ex. | name | $R_1$ | $R_2$ | $R_3$ | $R_4$ | $R_5$ | structure |
|---|---|---|---|---|---|---|---|
| 1 | [8R-(4bS*,8α,8aβ,12bβ)]-11-(N-Benzyl-N-isopropylaminocarbonyl)-7,10-dimethyl-1-methoxy-5,6,7,8,12,12b-hexahyrdo-(9H)-4,8-methanobenzofuro[3,2-e]pyrrolo[2,3-g]isoquinoline hydrochloride | Me | H | OMe | —O— | | 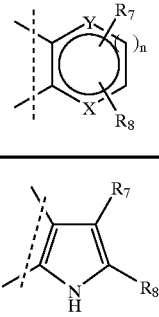 |
| 2 | [8R-(4bS*,8α,8aβ,12bβ)]-11-Diethylamminothiocarbonyl-7,10-dimethyl-1-methoxy-5,6,7,8,12,12b-hexahydro-(9H)-4,8-methanobenzofuro[3,2-e]pyrrolo[2,3-g]isoquinoline hydrochloride | Me | H | OMe | —O— | | 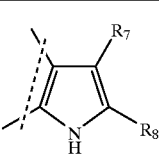 |
| 3 | [10R,4bS-(4bβ,9aβ)]-7-Diethylaminocarbonyl-8,14-dimethyl-4-hydroxy-4b,5,9,9a,10,11-hexahydro-(6H)-[2,3-h]pyrrolo[10,4-b]iminophenantrene | Me | H | H | OH | H | 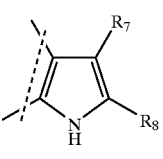 |
| 4 | [10R-4bS-(4bβ,9aβ)]-7-Diethylaminocarbonyl-3,4-dimethoxy-8,14-dimethyl-4b,5,9,9a,10,11-hexahydro-(6H)-[2,3-h]pyrrolo[10,4-b]iminophenantrene hydrochloride | Me | H | OMe | OMe | H | 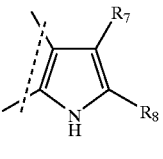 |
| 5 | [8R-(4bS*,8α,8aβ,12bβ)]-11-Diethylaminocarbonyl-1,8a-dimethoxy-7,10-dimethyl-5,6,7,8,12,12b-hexahydro-(9H)-4,8-methano benzofuro[3,2-e]pyrrolo[2,3-g]isoquinoline | Me | OMe | OMe | —O— | | 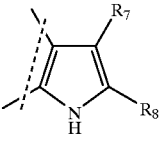 |
| 6 | [8R-(4bS*,8α,8aβ,12bβ]-7,10-dimethyl-11-etoxycarbonyl-5,6,7,8,12,12b-hexahydro-4,8-methanobenzofuro[3,2-3]pyrrolo[2,3-g]isoquinoline hydrochloride | Me | OH | OMe | —O— | | 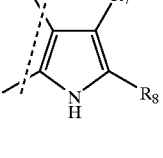 |

CHEMICAL TABLE-continued

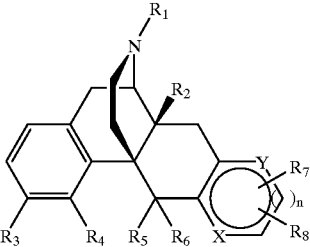

| # | Name | R1 | R2 | R3 | R4 | R5 | |
|---|------|----|----|----|----|----|---|
| 7 | [8R-(4bS*,8α,8aβ,12bβ)]-11-Diethylaminocarbonyl-8a-hydroxy-1-methoxy-10-methyl-7-(2-propenyl)-5,6,7,8,12,12b-hexahydro-(9H)-4,8-methanobenzofuro[3,2-e]pyrrolo[2,3-g]isoquinoline hydrochloride | Allyl | OH | OMe | —O— | | 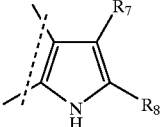 |
| 8 | [10R-4bS-(4bβ,9aβ)]-7-Diethylaminocarbonyl-8,14-dimethyl-3-methoxy-4-oxyphenyl-4b,5,9,9,a,10,11-hexahydro-(6H)-[2,3-h]pyrrolo[10,4-b]iminophenantrene | Me | H | OH | OPh | H | 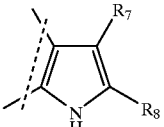 |
| 9 | [10R-4bS-(4bβ,9aβ)]-7-Diethylaminocarbonyl-8,14-dimethyl-3-methoxy-4b,5,9,9,a,10,11-hexahydro-(6H)-[2,3-h]pyrrolo[10,4b]iminophenantrene | Me | H | OMe | H | H | 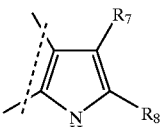 |
| 10 | [8R-(4bS*,8α,8aβ,12bβ)]-11-Etoxycarbonyl-7-methyl-1-methoxy-10-trifluoromethyl-5,6,7,8,12,12b-hexahydro-(9H)-4,8-methanobenzofuro[3,2-e]pyrrolo[2,3-g]isoquinoline | Me | H | OMe | —O— | | 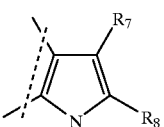 |
| 11 | [8R-(4bS*,8α,8aβ,12bβ)]-11-Etoxycarbonyl-7-methyl-10-(1-methylethyl)-1-methoxy-5,6,7,8,12,12b-hexahydro-(9H)-4,8-methanobenzofuro[3,2-e]pyrrolo[2,3-g]isoquinoline hydrochloride | Me | H | OMe | —O— | | 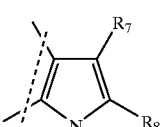 |
| 12 | [8R-(4bS*,8α,8aβ,12bβ)]-11-Diethylcarbonyl-10-methyl-1-methoxy-5,6,7,8,12,12b-hexahydro-(9H)-4,8-methanobenzofuro[3,2-e]pyrrolo[2,3-g]isoquinoline hydrochloride | H | H | OMe | —O— | | 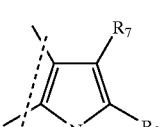 |
| 13 | [8R-(4bS*,8α,8aβ,12bβ)]-11-Benzoyl-7,10-dimethyl-1-methoxy-5,6,7,8,12,12b-hexahydro-(9H)-4,8-methanobenzofuro[3,2-e]pyrrolo[2,3-g]isoquinoline | Me | H | OMe | —O— | | 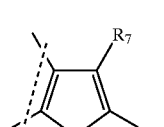 |
| 14 | [8R-(4bS*,8α,8aβ,12bβ)]-7,10-Dimethyl-1-methoxy-5,6,7,8,12,12b-hexahydro-4,8-methanobenzofuro[3,2-e]pyrrolo[2,3-g]isoquinoline-11-carboxy acid | Me | H | OMe | —O— | | 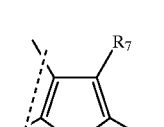 |

CHEMICAL TABLE-continued

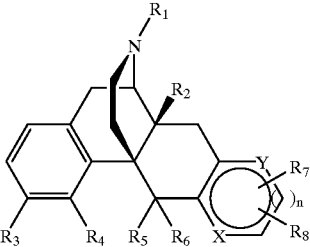

| | | | | | | |
|---|---|---|---|---|---|---|
| 15 | [8R-(4bS*,8α,8aβ,12bβ)-11-diethylaminocarbonyl-1-methoxy-10-methyl-7-(2-phenylethyl)-5,6,7,8,12,12b-hexahydro-(9H)-4,8-methanobenzofuro[3,2-e]pyrrolo[2,3-g]isoquinoline | Phenethyl | H | OMe | —O— | 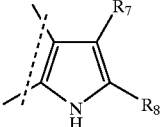 |
| 16 | [8R-(4bS*,8α,8aβ,12bβ)]-11-Diethylaminocarbonyl-7-ethyl-10-methyl-5,6,7,8,12,12b-hexahydro-(9H)-4,8-methanobenzofuro[3,2-e]pyrrolo[2,3-g]isoquinoline | Et | H | OMe | —O— | 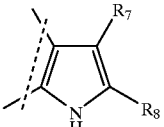 |
| 17 | [8R-(4bS*,8α,8aβ,12bβ)]-11-Acetyl-7,10-dimethyl-1-methoxy-11-(2-methylpropyl)ossicarbonyl-5,6,7,8,12,12b-hexahydro-[9H]-4,8-methanobenzofuro[3,2-e]pyrrolo[2,3-g]isoquinoline | Me | H | OMe | —O— | 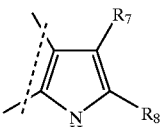 |
| 18 | [8R-(4bS*,8α,8aβ,12bβ)]-11-Isobutilcarbonyl-7,10-dimethyl-1-methoxy-5,6,7,8,12,12b-hexahydro-[9H]-4,8-methanobenzofuro[3,2-e]pyrrolo[2,3-g]isoquinoline hydrochloride | Me | H | OMe | —O— | 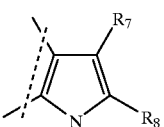 |
| 19 | [8R-(4bS*,8α,8aβ,12bβ)]-7-Benzil-11-diethylaminocarbonyl-10-methyl-1-methoxy-5,6,7,8,12,12b-hexahydro-[9H]-4,8-methanobenzofuro[3,2-e]pyrrolo[2,3-g]isoquinoline | benzil | H | OMe | —O— | 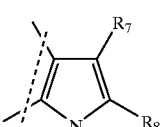 |
| 20 | [8R-(4bS*,8α,8aβ,12bβ)]-11-Diethylaminocarbonyl-7-isopropyl-10-methyl-1-methoxy-5,6,7,8,12,12b-hexahydro-[9H]-4,8-methanobenzofuro[3,2-e]pyrrolo[2,3-g]isoquinoline | i-Pr | H | OMe | —O— | 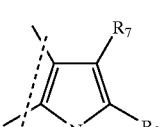 |
| 21 | [8R-(4bS*,8α,8aβ,12bβ)]-11-Diethylaminocarbonyl-10-methyl-1-methoxy-7-isopropyl-5,6,7,8,12,12b-hexahydro-[9H]-4,8-methanobenzofuro[3,2-e]pyrrolo[2,3-g]isoquinoline hydrochloride | Pr | H | OMe | —O— | 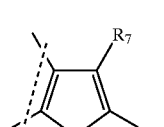 |
| 22 | [8R-(4bS*,8α,8aβ,12bβ)]-11-Diisopropylaminocarbonyl-7,10-dimethyl-1-ethoxy-5,6,7,8,12,12b-hexahydro-[9H]-4,8-methanobenzofuro[3,2-e]pyrrolo[2,3-g]isoquinoline hydrochloride | Me | H | OEt | —O— | 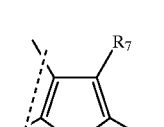 |

CHEMICAL TABLE-continued

| # | Name | R₁ | R₂ | R₃ | R₄ | Ring |
|---|------|----|----|----|----|------|
| 23 | [8R-(4bS*,8α,8aβ,12bβ)]-11-Diisopropylaminocarbonyl-7,10-dimethyl-1-isopropyloxy-5,6,7,8,12,12b-hexahydro-[9H]-4,8-methanobenzofuro[3,2-e]pyrrolo[2,3-g]isoquinoline hydrochloride | Me | H | O-i-Pr | —O— | pyrrole |
| 24 | [8R-(4bS*,8α,8aβ,12bβ)]-11-Diisopropylaminocarbonyl-7-methyl-1-methoxy-10-trifluoromethyl-5,6,7,8,12,12b-hexahydro-[9H]-4,8-methanobenzofuro[3,2-e]pyrrolo[2,3-g]isoquinoline | Me | H | OMe | —O— | pyrrole |
| 25 | [8R-(4bS*,8α,8aβ,12bβ)]-7-Allyl-11-isobuthylcarbonyl-10-methyl-1-methoxy-5,6,7,8,12,12b-hexahydro-4,8-methanobenzofuro[3,2-e]pyrrolo[2,3-g]isoquinoline-(9H)-8a-ol hydrochloride | Allyl | OH | OMe | —O— | pyrrole |
| 26 | [8R-(4bS*,8α,8aβ,12bβ)]-7-Allyl-11-isobuthylcarbonyl-10-methyl-5,6,7,8,12,12b-hexahydro-4,8-methanobenzofuro[3,2-e]pyrrolo[2,3-g]isoquinoline-1,8a(9H)-diol hydrochloride | Allyl | OH | OH | —O— | pyrrole |
| 27 | [8R-(4bS*,8α,8aβ,12bβ)]-7-Allyl-11-isobuthylcarbonyl-1-ethoxy-10-methyl-5,6,7,8,12,12b-hexahydro-4,8-methanobenzofuro[3,2-e]pyrrolo[2,3-g]isoquinoline-(9H)-8a-ol hydrochloride | Allyl | OH | OEt | —O— | pyrrole |
| 28 | [8R-(4bS*,8α,8aβ,12bβ)]-11-Diisopropylaminocarbonyl-7,10-dimethyl-1-ethyl-5,6,7,8,12,12b-hexahydro-[9H]-4,8-methanobenzofuro[3,2-e]pyrrolo[2,3-g]isoquinoline hydrochloride | Me | H | Et | —O— | pyrrole |
| 29 | [8R-(4bS*,8α,8aβ,12bβ)]-7,10-dimethyl-1-methoxy-11(3-methyl-1,2,4-oxadiazole-5-yl)-5,6,7,8,12,12b-hexahydro-[9H]-4,8-methanobenzofuro[3,2-e]pyrrolo[2,3-g]isoquinoline | Me | H | OMe | —O— | pyrrole |
| 30 | [8R-(4bS*,8α,8aβ,12bβ)]-1-Bromo-11-diisopropylaminocarbonyl-7,10-dimethyl-5,6,7,8,12,12b-hexahydro-[9H]-4,8-methanobenzofuro[3,2-e]pyrolo[2,3-g]isoquinolin-8a-(9H)-ol hydrochloride | Me | OH | Br | —O— | pyrrole |

CHEMICAL TABLE-continued

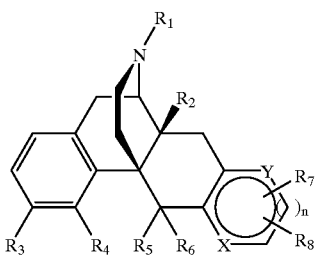

| | | R₁ | R₂ | R₃ | X | Y | |
|---|---|---|---|---|---|---|---|
| 31 | [8R-(4bS*,8α,8aβ,12bβ)]-11-Ethoxycarbonyl-10-ethoxycarbonyl methylen-1-methoxy-7-methyl-5,6,7,8,12,12b-hexahydro-[9H]-4,8-methanobenzofuro[3,2-e]pyrrolo[2,3-g]isoquinolin-8a-(9H)-ol hydrochloride | Me | H | OMe | —O— | | 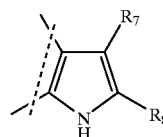 |
| 32 | [8R-(4bS*,8α,8aβ,12bβ)]-7,10-Dimethyl-1-methoxy-11-tertbuthylcarbonyl-5,6,7,8,12,12b-hexahydro-[9H]-4,8-methanobenzofuro[3,2-e]pyrrolo[2,3-g]isoquinoline hydrochloride | Me | H | OMe | —O— | | 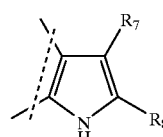 |
| 33 | [8R-(4bS*,8α,8aβ,12bβ)]-1-Bromo-11-diisopropylaminocarbonyl-7,10-dimethyl-5,6,7,8,12,12b-hexahydro-[9H]-4,8-methanobenzofuro[3,2-e]pyrrolo[2,3-g]isoquinoline hydrochloride | Me | H | Br | —O— | | 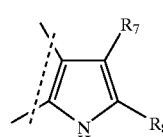 |
| 34 | [8R-(4bS*,8α,8aβ,12bβ)]-11-isopropylcarbonyl-7,10-dimethyl-1-methoxy-5,6,7,8,12,12b-hexahydro-[9H]-4,8-methanobenzofuro[3,2-e]pyrrolo[2,3-g]isoquinoline hydrochloride | Me | H | OMe | —O— | | 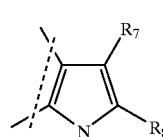 |
| 35 | [8R-(4bS*,8α,8aβ,12bβ)]-1-Bromo-7,10-dimethyl-11-isobuthylcarbonyl-hexahydro-[9H]-4,8-methanobenzofuro[3,2-e]pyrrolo[2,3-g]isoquinoline hydrochloride | Me | H | Br | —O— | | 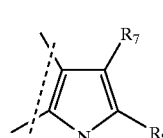 |
| 36 | [10R,4bS-(4bβ,9aα)]-7diisopropylaminocarbonyl-8,14-dimethyl-4b,5,9,9a,10,11-hexahydro-[6H]-10,4b-(iminoethano)phenantro[3,2-b]pyrrole | Me | H | H | H | H | 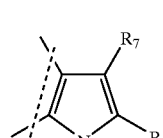 |
| 37 | [8R-(4bS*,8α,8aβ,12bβ)]-7,10-Dimethyl-1-methoxy-11-(2-propyl)oxycarbonyl-5,6,7,8,12,12b-hexahydro-[9H]-4,8-methanolbenzofuro[3,2-e]pyrrolo[2,3-g]isoquinoline hydrochloride | Me | H | OMe | —O— | | 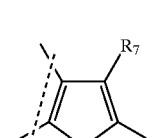 |
| 38 | [8R-(4bS*,8α,8aβ,12bβ)]-7,10-Dimethyl-11-(1,1-dimethylethyl)oxycarbonyl-1-methoxy-5,6,7,8,12,12b-hexahydro-[9H]-4,8-methanobenzofuro[3,2-e]pyrrolo[2,3-g]isoquinoline hydrochloride | Me | H | OMe | —O— | | 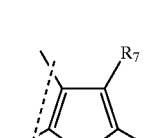 |

CHEMICAL TABLE-continued

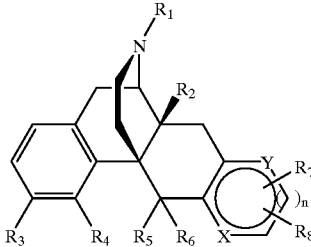

| | | R₁ | R₂ | R₃ | R₄, R₅ | R₆ | |
|---|---|---|---|---|---|---|---|
| 39 | [8R-(4bS*,8α,8aβ,12bβ)]-7,10-Dimethyl-11-methoxycarbonyl-1-methoxy-11-5,6,7,8,12,12b-hexahydro-[9H]-4,8-methanobenzofuro[3,2-e]pyrrol[2,3-g]isoquinoline hydrochloride | Me | H | OMe | —O— | | 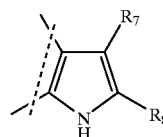 |
| 40 | [8R-(4bS*,8α,8aβ,12bβ)]-7,10-Dimethyl-1-methoxy-11-(1-propyl)oxycarbonyl-5,6,7,8,12,12b-hexahydro-[9H]-4,8-methanobenzofuro[3,2-e]pyrrolo[2,3-g]isoquinoline hydrochloride | Me | H | OMe | —O— | | 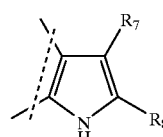 |
| 41 | [8R-(4bS*,8α,8aβ,12bβ)]-1-Acetyl-7,10-dimethyl-5,6,7,8,12,12b-hexahydro-[9H]-11-isobuthylcarbonyl-4,8-methanobenzofuro[3,2-e]pyrrolo[2,3-g]isoquinoline hydrochloride | Me | H | COMe | —O— | | 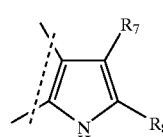 |
| 42 | [8R-(4bS*,8α,8aβ,12bβ)]-11-Ethyloxayl-7,10-dimethyl-1-methoxy-5,6,7,8,12,12b-hexahydro-[9H]-4,8-methanobenzofuro[3,2-e]pyrrolo[2,3-g]isoquinoline hydrochloride | Me | H | OMe | —O— | | 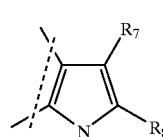 |
| 43 | [10R,4bS-(4bβ,9aα)]-7-Isobuthylcarbonyl-8,14-dimethyl-4-hydroxy-3-methoxy-4b,5,9,9a,10,11-hexahydro-[6H]-10,4b-(iminoethano)phenantro[3,2-b]pyrrole hydrochloride | Me | H | OMe | OH | H | 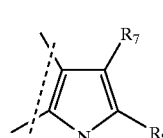 |
| 44 | [10R,4bS-(4bβ,9aα)]-14-Allyl-7-isobuthylcarbonyl-4-hydroxy-8-methyl-3-methoxy-4b,5,8,8a,10,11-hexahydro-[6H]-10,4b-(iminoethano)penantro[3,2-b]pyrrole-9a-ol hydrochloride | Allyl | OH | OMe | OH | H | 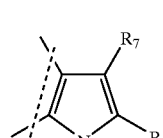 |
| 45 | [8R-(4bS*,8α,8aβ,12bβ)]-7-Allyl-11-isobuthylcarbonyl-1-methoxy-10-methyl-5,6,7,8,12,12b-hexahydro-[9H]-4,8-methanobenzofuro[3,2-e]pyrrolo[2,3-g]isoquinoline hydrochloride | Allyl | H | OMe | —O— | | 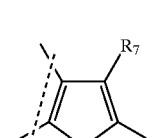 |
| 46 | [10R,4bS-(4bβ,9aα)]-4-Acetoxy-7-diisopropylaminocarbonyl-8,14,dimethyl-3-methoxy-4b,5,9,9a,10,11-hexahydro-[6H]-10,4b-(iminoethano)phenantro[3,2-b]pyrrole | Me | H | OMe | OAc | H | 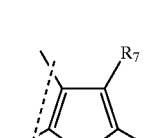 |

CHEMICAL TABLE-continued

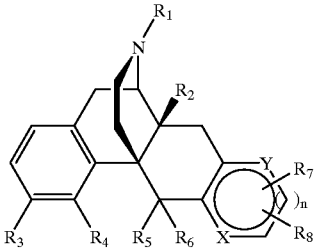

| | | R1 | R2 | R3-R4 | R5 | R6 | |
|---|---|---|---|---|---|---|---|
| 47 | [10R,4bS-(4bβ,9aα)]-14-Allyl-7-isobuthylcarbonyl-8-methyl-3-methoxy-4b,5,9,9a,10,11-hexahydro-[6H]-10,4b-(iminoethano)phenantro[3,2-b]pyrrole-9a-ol hydrochloride | Allyl | OH | —OCH$_2$O— | | H | 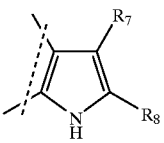 |
| 48 | [8R-(4bS*,8α,8aβ,12bβ)]-7,10-Dimethyl-1-methoxy-11-(penthyl-3-carbonyl)-5,6,7,8,12,12b-hexahydro-[9H]-4,8-methanobenzofuro[3,2-e]pyrrolo[2,3-g]isoquinoline hydrochloride | Me | H | OMe | —O— | | 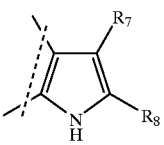 |
| 49 | [8R-(4bS*,8α,8aβ,12bβ)]-11-Isopropylcarbonyl-7,10,12-trimethyl-1-methoxy-5,6,7,7,12,12b-hexahydro-[9H]-4,8-methanobenzofuro[3,2-e]pyrrolo[2,3-g]isoquinoline hydrochloride | Me | H | OMe | —O— | | 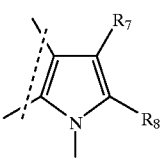 |
| 50 | [8R-(4bS*,8α,8aβ,12bβ)]-11-Diisopropylaminocarbonyl-7,10-dimethyl-1-methoxy-5,6,7,8,12,12b-hexahydro-[9H]-4,8-methanobenzofuro[3,2-e]pyrrolo[2,3-g]isoquinoline-8a-(9H)-ol hydrochloride | Me | OH | OMe | —O— | | 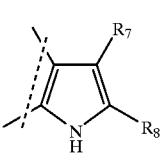 |
| 51 | [8R-(4bS*,8α,8aβ,12bβ)]-7,10,11-trimethyl-1-methoxy-5,6,7,8,12,12b-hexahydro-[9H]-4,8-methanobenzofuro[3,2-e]pyrrolo[2,3-g]isoquinoline hydrochloride | Me | H | OMe | —O— | | 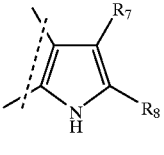 |
| 52 | [8R-(4bS*,8α,8aβ,12bβ)]-3-Bromo-7-diisopropylaminocarbonyl-8,14-dimethyl-1-methoxy-4b,5,9,9a,10,11-hexahydro-4-hydroxy-[6H]-10,4b-(iminoethano)phenantro[3,2-b]pyrrole | Me | H | Br | OH | H | 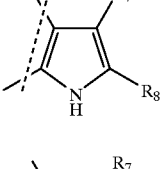 |
| 53 | [8R-(4bS*,8α,8aβ,12bβ)]-11-isopropylethanolaminocarbonyl-7,10-dimethyl-1-methoxy-5,6,7,8,12,12b-hexahydro-[9H]-4,8-methanobenzofuro[3,2-e]pyrrolo[2,3-g]isoquinoline | Me | H | OMe | —O— | | 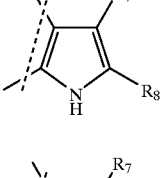 |
| 54 | [8R-(4bS*,8α,8aβ,12bβ)]-7-Allyl-11-disopropylaminocarbonyl-10-methyl-1-methoxy-5,6,7,8,12,12b-hexahydro-[9H]-4,8-methanobenzofuro[3,2-e]pyrrolo[2,3-g]isoquinoline | Allyl | H | OMe | —O— | | 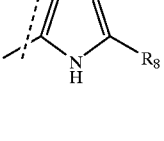 |

CHEMICAL TABLE-continued

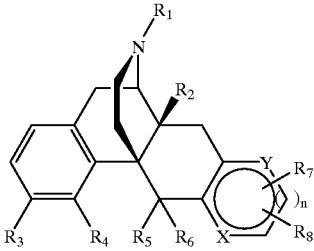

| # | Name | R1 | R2 | R3 | R4 | R5 | Ring |
|---|------|----|----|----|----|----|------|
| 55 | [8R-(4bS*,8α,8aβ,12bβ)]-7-isobuthylcarbonyl-3-methoxy-8,14-dimethyl-4b,5,9,9a,10,11-hexahydro-4-hydroxy[6H]-10,4b-(iminoethano)phenantro[3,2-b]pyrrole | Me | H | OMe | OH | H | 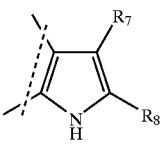 |
| 56 | [8R-(4bS*,8α,8aβ,12bβ)]-11-Disopropylaminocarbonyl-7-hydroxyethyl-1-methoxy-10-methyl-5,6,7,8,12,12b-hexahydro-[9H]-4,8-methanobenzofuro[3,2-e]pyrrolo[2,3-g]isoquinoline | $(CH_3)_3OH$ | H | OMe | —O— | | 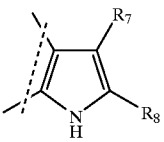 |
| 57 | [8R-(4bS*,8α,8aβ,12bβ)]-11-carboxamido-7,10-dimethyl-1-methoxy-5,6,7,8,12,12b-hexahydro-[9H]-4,8-methano benzofuro[3,2-e]pyrrolo[2,3-g]isoquinoline | Me | H | OMe | —O— | | 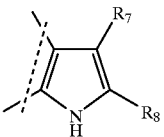 |
| 58 | [8R-(4bS*,8α,8aβ,12bβ)]-11-(N-Benzyl-N-isopropyl)amino carbonyl-7,10-dimethyl-1-methoxy-5,6,7,8,12,12b-hexahydro-[9H]-4,8-methano benzofuro[3,2-e]pyrrolo[2,3-g]isoquinoline-8a-(9H)-ol hydrochloride | Me | OH | OMe | —O— | | 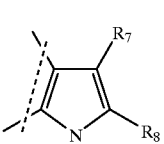 |
| 59 | [8R-(4bS*,8α,8aβ,12bβ)]-11-Isopropylethanoaminocarbonyl-8,14-dimethyl-4-hydroxy-3-methoxy-4b,5,9,9a,10,11-hexahydro-[6H]-[2,3-h]pyrrolo-[10,4b]-iminoethanophenantrene | Me | H | OMe | OH | H | 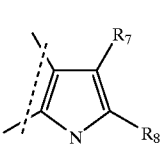 |
| 60 | [8R-(4bS*,8α,8aβ,12bβ)]-11-Benzoyloxycarbonyl-7,10-dimethyl-1-methoxy-5,6,7,8,12,12b-hexahydro-[9H]-4,8-methano benzofuro[3,2-e]pyrrolo[2,3-g]isoquinoline hydrochloride | Me | H | OMe | —O— | | 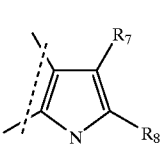 |
| 61 | [8R-(4bS*,8α,8aβ,12bβ)]-1-Acetyl-7,10-dimethyl-5,6,7,8,12,12b-hexahydro-[9H]-11-(2-methylpropyl)oxycarbonyl-4,8-methanobenzofuro[3,2-e]pyrrolo[2,3-g]isoquinoline hydrochloride | Me | H | COMe | —O— | | 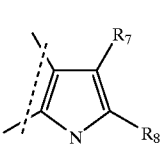 |
| 62 | [8R-(4bS*,8α,8aβ,12bβ)]-11-Diisopropylaminocarbonyl-7,10,12-trimethyl-1-methoxy-5,6,7,8,12,12b-hexahydro-[9H]-4,8-methanobenzofuro[3,2-e]pyrrolo[2,3-g]isoquinoline hydrochloride | Me | H | OMe | —O— | | 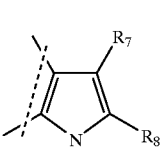 |

CHEMICAL TABLE-continued

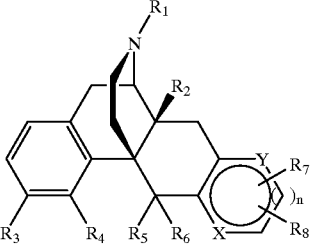

| | | R1 | R2 | R3 | R5 R6 | R7 R8 |
|---|---|---|---|---|---|---|
| 63 | [8R-(4bS*,8α,8aβ,12bβ)]-11-(2,4-dimethyl-3-pentyloxy)carbonyl-7,10-dimethyl-1-methoxy-5,6,7,8,12,12b-hexahydro-[9H]-4,8-methano benzofuro[3,2-e]pyrrolo[2,3-g]isoquinoline | Me | H | OMe | —O— | 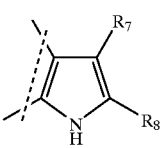 |
| 64 | [8R-(4bS*,8α,8aβ,12bβ)]-1-Bromo-7,10-dimethyl-5,6,7,8,12,12b-hexahydro-[9H]-11-(2-methylpropyl)oxycarbonyl 4,8-methanobenzofuro[3,2-e]pyrrolo[2,3-g]isoquinoline | Me | H | Br | —O— | 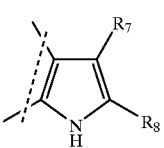 |
| 65 | [10R-4bS-(4bβ,9aβ)]-8,10-Dimethyl-4b,5,9,9a,10,11-hexahydro-[9H]-7-(2-methylpropyl)oxycarbonyl-10,4b-(iminoethano)phenantro[3,2-b]pyrrole hydrochloride | Me | H | H | H H | 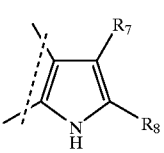 |
| 66 | [8R-(4bS*,8α,8aβ,12bβ)]-7-Ethoxycarbonylmethylen-11-diisopropylaminocarbonyl-1-methoxy-10-methyl-5,6,7,8,12,12b-hexahydro-[9H]-4,8-methanobenzofuro[3,2-e]pyrrolo[2,3-g]isoquinoline hydrochloride | CH3COOEt | H | OMe | —O— | 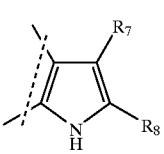 |
| 67 | [8R-(4bS*,8α,8aβ,12bβ)]-7-Oxycarbonylmethylen-11-diisopropylaminocarbonyl-1-methoxy-10-methyl-5,6,7,8,12,12b-hexahydro-[9H]-4,8-methanobenzofuro[3,2-e]pyrrolo[2,3-g]isoquinoline | CH3COOH | H | OMe | —O— | 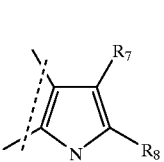 |
| 68 | [8R-(4bS*,8α,8aβ,12bβ)]-7,10-Dimethyl-11-dimethylamino carbonyl-1-methoxy-10-methyl-5,6,7,8,12,12b-hexahydro-[9H]-4,8-methanobenzofuro[3,2-e]pyrrolo[2,3-g]isoquinoline hydrochloride | Me | H | OMe | —O— | 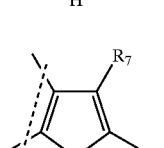 |
| 69 | [10R-4bS-(4bβ,9aβ)]-8,14-Dimethyl-7-isobutyloxycarbonyl-3-methoxy-4b,5,9,9a,10,11-hexahydro-[6H]-[2,3-h]pyrrolo[10,4b]-iminoethanophenantrene hydrochloride | Me | H | OMe | H H | 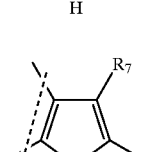 |
| 70 | [8R-(4bS*,8α,8aβ,12bβ)]-11-Diisopropylaminocarbonyl-1-methoxy-10-methyl-5,6,7,8,12,12b-hexahydro-[9H]-11-(2-methylpropyl)oxycarbonyl-4,8-methanobenzofuro[3,2-e]pyrrolo[2,3-g]isoquinoline | H | H | OMe | —O— | 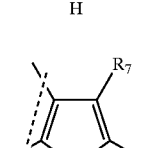 |

CHEMICAL TABLE-continued

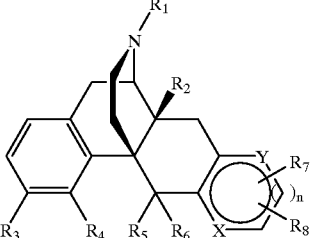

| # | Name | R₁ | R₂ | R₃ | R₄ R₅ R₆ | X | Structure |
|---|------|----|----|----|----|----|----|
| 71 | [8R-(4bS*,8α,8aβ,12bβ)]-1-methoxy-7-methyl-10-oxycarbonyl-11-oxycarbonyl-5,6,7,8,12,12b-hexahydro-[9H]-4,8-methanobenzofuro[3,2-e]pyrrolo[2,3-g]isoquinoline | Me | H | OMe | | —O— | 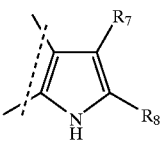 |
| 72 | [8R-(4bS*,8α,8aβ,12bβ)]-7-Aminocarbonylmethyl-11-diisopropylaminocarbonyl-1-methoxy-10-methyl-5,6,7,8,12,12b-hexahydro-[9H]-4,8-methanobenzofuro[3,2-e]pyrrolo[2,3-g]isoquinoline | CH₂CONH₂ | H | OMe | | —O— | 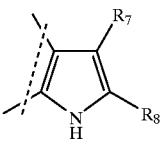 |
| 73 | [8R-(4bS*,8α,8aβ,12b-11-diisopropylaminotiocarbonyl-1-methoxy-7,10-dimethyl-5,6,7,8,12,12b-hexahydro-[9H]-4,8-methanobenzofuro[3,2-e]pyrrolo[2,3-g]isoquinoline | Me | H | OMe | | —O— | 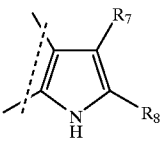 |
| 74 | [[8R-(4bS*,8α,8aβ,12b-7,10-dimethyl-1-methoxy-11-(2-methylpropyl)oxycarbonyl-5,6,7,8,12,12b-hexahydro-[9H]-4,8-methanobenzofuro[3,2-e]pyrrolo[2,3-g]isoquinolin-12-yl] acetic acid hydrochloride | Me | H | OMe | | —O— | 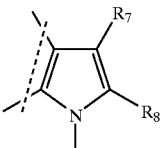 |
| 75 | [10R,4bS-(4bβ,9aβ)]-7-Diisopropylaminocarbonyl-8,14-dimethyl-4b,59,9a,10,11-hexahydro-9a-hydroxy-[6H]-10,4b-(iminoethano)phenantro[3,2-b]pyrrole | Me | OH | H | H H | | 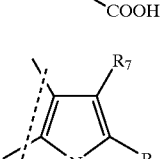 |
| 76 | [10R,4bS-(4bβ,9aβ)]-8,14-dimethyl-4b,59,9a,10,11-hexahydro-9a-hydroxy-7-(2-methylpropyl)oxycarbonyl-10,4b-(iminoethano)phenantro[3,2-b]pyrrole hydrochloride | Me | OH | H | H H | | 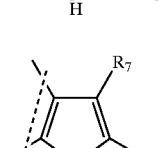 |
| 77 | [10R,4bS-(4bβ,9aβ)]-14-Allyl-7-diisopropylcarbonyl-4b,59,9a,10,11-hexahydro-9a-hydroxy-10,4b-(iminoethano)phenantro[3,2-b]pyrrole hydrochloride | Allyl | OH | H | H H | | 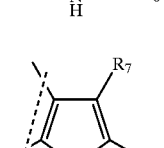 |
| 78 | [8R-(4bS*,8α,8aβ,12bβ)-7-Allyl-11-diisopropylaminotiocarbonyl-1-ethoxy-10-methyl-5,6,7,8,12,12b-hexahydro-[9H]-4,8-methanobenzofuro[3,2-e]pyrrolo[2,3-g]isoquinolin-8a-ol hydrochloride | Allyl | OH | OEt | | —O— | 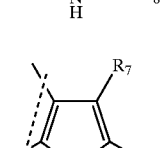 |

CHEMICAL TABLE-continued

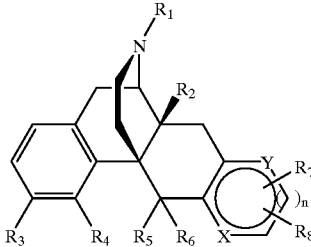

| # | Name | R1 | R2 | R3/R4 | X-Y | Ring |
|---|------|----|----|-------|-----|------|
| 79 | [[8R-(4bS*,8α,8aβ,12bβ)-11-diisopropylaminocarbonyl-7,10-dimethyl-1-methoxy-5,6,7,8,12,12b-hexahydro-[9H]-4,8-methanobenzofuro[3,2-e]pyrrolo[2,3-g]isoquinolin-12-yl] acetic acid hydrochloride | Me | H | OMe | —O— | 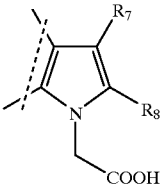 |
| 80 | [[8R-(4bS*,8α,8aβ,12bβ)-11-(N-Benzyl-N-isopropyl)amino carbonyl-7,10-dimethyl-1-methoxy-5,6,7,8,12,12b-hexahydro-[9H]-4,8-methano benzofuro[3,2-e]pyrrolo[2,3-g]isoquinolin-12-yl]acetic acid hydrochloride | Me | H | OMe | —O— | 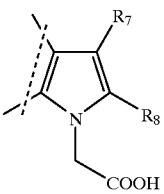 |
| 81 | [[8R-(4bS*,8α,8aβ,12bβ)-7-Allyl-11-(2-methylpropyl)oxy carbonyl-1-ethoxy-5,6,7,8,12,12b-hexahydro-[9H]-4,8-methano benzofuro[3,2-e]pyrrolo[2,3-g]isoquinolin-8a-ol hydrochloride | Allyl | OH | OEt | —O— | 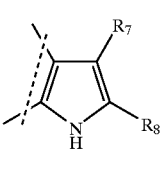 |
| 82 | [[8R-(4bS*,8α,8aβ,12bβ)-7,10,12-trimethyl-1-mthoxy-11-methyloxycarbonyl-5,6,7,8,12,12b-hexahydro-[9H]-4,8-methano benzofuro[3,2-e]pyrrolo[2,3-g]isoquinoline | Me | H | OMe | —O— | 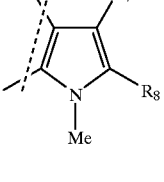 |
| 83 | [[8R-(4bS*,8α,8aβ,12bβ)-11-Diisopropylaminocarbonyl-7-acetoxy-10-methyl-1-methoxy-5,6,7,8,12,12b-hexahydro-[9H]-4,8-methano benzofuro[3,2-e]pyrrolo[2,3-g]isoquinoline | COMe | H | OMe | —O— | 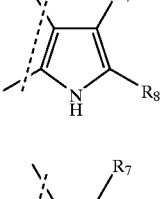 |
| 84 | [[8R-(4bS*,8α,8aβ,12bβ)-11-Diisopropylaminocarbonyl-4,8-diacetoxy-14-methyl-3-methoxy-4b,5,9,9a,10,11-hexahydro-[6H]-[2,3-h]pyrrolo[10,11-b]iminoethanophenantrene | COMe | H | OMe | OH H— | 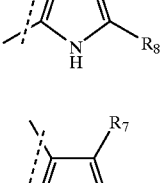 |
| 85 | Ethyl-[[8R-(4bS*,8α,8aβ,12bβ)-7,10-dimethyl-1-methoxy-11-(2-methylpropyl)oxycarbonyl-5,6,7,8,12,12b-hexahydro-[9H]-4,8-methano benzofuro[3,2-e]pyrrolo[2,3-g]isoquinolin-12-yl] acetate hydrochloride | Me | H | OMe | —O— | 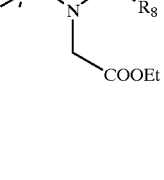 |

CHEMICAL TABLE-continued

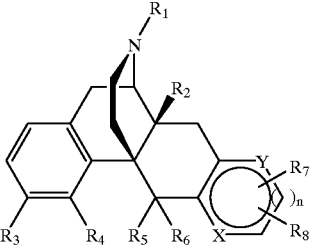

| | | R$_1$ | R$_2$ | R$_3$ | X-Y | |
|---|---|---|---|---|---|---|
| 86 | N-Benzyl-[[8R-(4bS*,8α,8aβ,12bβ)-7,10-dimethyl-1-methoxy-11-(2-methylpropyl)oxycarbonyl-5,6,7,8,12,12b-hexahydro-[9H]-4,8-methano benzofuro[3,2-e]pyrrolo[2,3-g]isoquinolin-12-yl] acetamide hydrochloride | Me | H | OMe | —O— | 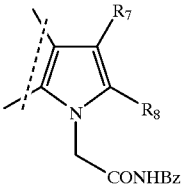 |
| 87 | Ethyl-[[8R-(4bS*,8α,8aβ,12bβ)-11-diisopropylaminocarbonyl-7,10-dimethyl-1-methoxy-5,6,7,8,12,12b-hexahydro-[9H]-4,8-methano benzofuro[3,2-e]pyrrolo[2,3-g]isoquinolin-12-yl] acetate | Me | H | OMe | —O— | 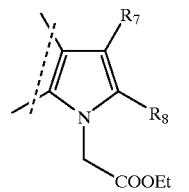 |
| 88 | Ethyl-[[8R-(4bS*,8α,8aβ,12bβ)-11-isobuthylcarbonyl-7,10,12-trimethyl-1-methoxy-5,6,7,8,12,12b-hexahydro-[9H]-4,8-methanobenzofuro[3,2-e]pyrrolo[2,3-g]isoquinoline | Me | H | OMe | —O— | 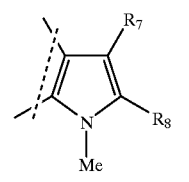 |
| 89 | Ethyl-[[8R-(4bS*,8α,8aβ,12bβ)-11-Diethylphosphonoyl-7,10-dimethyl-1-methoxy-5,6,7,8,12,12b-hexahydro-[9H]-4,8-methanobenzofuro[3,2-e]pyrrolo[2,3-g]isoquinoline | Me | H | OMe | —O— | 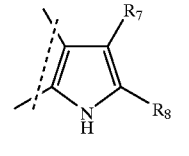 |
| 90 | [8R-(4bS*,8α,8aβ,12bβ)]-11-[(2,2,2-trifluoroethyl)-isopropylamino]carbonyl-7,10-dimethyl-1-methoxy-5,6,7,8,12,12b-hexahydro-[9H]-4,8-methano benzofuro[3,2-e]pyrrolo[2,3-g]isoquinoline | Me | H | OMe | —O— | 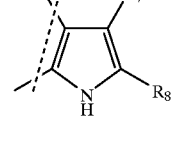 |
| 91 | [8R-(4bS*,8α,8aβ,12bβ)]-10-methyl-1-methoxy-11-(2-methylpropyl)oxycarbonyl-5,6,7,8,12,12b-hexahydro-[9H]-4,8-methano benzofuro[3,2-e]pyrrolo[2,3-g]isoquinoline hydrochloride | H | H | OMe | —O— | 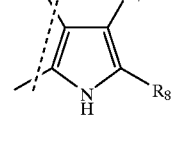 |
| 92 | [8R-(4bS*,8α,8aβ,12bβ)]-7,10-Dimethyl-1-hydroxy-11-(2-methylpropyl)oxycarbonyl-5,6,7,8,12,12b-hexahydro-[9H]-4,8-methano benzofuro[3,2-e]pyrrolo[2,3-g]isoquinoline hydrochloride | Me | H | OH | —O— | 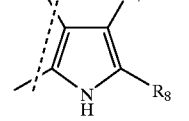 |

CHEMICAL TABLE-continued

| | | $R_1$ | $R_2$ | | | |
|---|---|---|---|---|---|---|
| 93 | [[8R-(4bS*,8α,8aβ,12bβ)]-7-Allyl-11-(2-methylpropyl)oxycarbonyl-8a-hydroxy-10-methyl-5,6,7,8,12,12b-hexahydro-[9H]-4,8-methanobenzofuro[3,2-e]pyrrolo[2,3-g](1-isoquinolinyloxy)]acetic acid | Allyl | OH | —O—CH₂—C(=O)—OH | —O— | pyrrole with $R_7$, $R_8$, NH |
| 94 | N-Methyl-[8R-(4bS*,8α,8aβ,12bβ)]-7,10-dimethyl-1methoxy--11-(methylpropyl)oxycarbonyl-5,6,7,8,12,12b-hexahydro-[9H]-4,8-methanobenzofuro[3,2-e]pyrrolo[2,3-g]isoquinolin-12-yl]acetamide hydrochloride | Me | H | OMe | —O— | pyrrole with $R_7$, $R_8$, N–CH₂CONHMe |
| 95 | N,N-Dimethyl-[8R-(4bS*,8α,8aβ,12bβ)]-7,10-dimethyl-1methoxy--11-(methylpropyl)oxycarbonyl-5,6,7,8,12,12b-hexahydro-[9H]-4,8-methanobenzofuro[3,2-e]pyrrolo[2,3-g]isoquinolin-12-yl]acetamide hydrochloride | Me | H | OMe | —O— | pyrrole with $R_7$, $R_8$, N–CH₂CONHMe₂ |
| 96 | [8R-(4bS*,8α,8aβ,12bβ)]-7,10-dimethyl-1methoxy--11-(pyrrolidin-1-yl)carbonyl-5,6,7,8,12,12b-hexahydro-[9H]-4,8-methanobenzofuro[3,2-e]pyrrolo[2,3-g]isoquinoline hydrochloride | Me | H | OMe | —O— | pyrrole with $R_7$, $R_8$, NH |
| 97 | [8R-(4bS*,8α,8aβ,12bβ)]-7,10-dimethyl-1methoxy--11-(piperidin-1-yl)carbonyl-5,6,7,8,12,12b-hexahydro-[9H]-4,8-methanobenzofuro[3,2-e]pyrrolo[2,3-g]isoquinoline hydrochloride | Me | H | OMe | —O— | pyrrole with $R_7$, $R_8$, NH |
| 98 | [8R-(4bS*,8α,8aβ,12bβ)]-7,10-dimethyl-1methoxy--11-(morpholi-4-yl)carbonyl-5,6,7,8,12,12b-hexahydro-[9H]-4,8-methanobenzofuro[3,2-e]pyrrolo[2,3-g]isoquinoline hydrochloride | Me | H | OMe | —O— | pyrrole with $R_7$, $R_8$, NH |
| 99 | [8R-(4bS*,8α,8aβ,12bβ)]-7,10-dimethyl-1-methoxy-11-(4-methyl-piperazin-1-yl)carbonyl-5,6,7,8,12,12b-hexahydro-[9H]-4,8-methanobenzofuro[3,2-e]pyrrolo[2,3-g]isoquinoline | Me | H | OMe | —O— | pyrrole with $R_7$, $R_8$, NH |

CHEMICAL TABLE-continued

| | | R₂ | | | | |
|---|---|---|---|---|---|---|
| 100 | [8R-(4bS*,8α,8aβ,12bβ)]-7,10-dimethyl-1-methoxy-11-(4-(2-hydroxyethyl)-piperazin-1-yl)carbonyl-5,6,7,8,12,12b-hexahydro-[9H]-4,8-methano benzofuro[3,2-e]pyrrolo[2,3-g]isoquinoline dihydrochloride | Me | H | OMe | —O— | pyrrole with R₇, R₈, NH |
| 101 | [8R-(4bS*,8α,8aβ,12bβ)]-7,10-dimethyl-11-[N-(4-ethoxycarbonyl)phenylmethyl-N-isopropyl]aminocarbonyl-1-methoxy-5,6,7,8,12,12b-hexahydro-[9H]-4,8-methano benzofuro[3,2-e]pyrrolo[2,3-g]isoquinoline hydrochloride | Me | H | OMe | —O— | pyrrole with R₇, R₈, NH |
| 102 | [8R-(4bS*,8α,8aβ,12bβ)]-7,10-dimethyl-1-methoxy-11-[N-(4-carboxy)phenylmethyl-N-isopropyl]aminocarbonyl-1-methoxy-5,6,7,8,12,12b-hexahydro-[9H]-4,8-methano benzofuro[3,2-e]pyrrolo[2,3-g]isoquinoline | Me | H | OMe | —O— | pyrrole with R₇, R₈, NH |
| 103 | [8R-(4bS*,8α,8aβ,12bβ)]-7,10-dimethyl-1-methoxy-11-[N-(3-ethoxycarbonyl)phenylmethyl-N-isopropyl]aminocarbonyl-1-methoxy-5,6,7,8,12,12b-hexahydro-[9H]-4,8-methano benzofuro[3,2-e]pyrrolo[2,3-g]isoquinoline hydrochloride | Me | H | OMe | —O— | pyrrole with R₇, R₈, NH |
| 104 | [8R-(4bS*,8α,8aβ,12bβ)]-7,10-dimethyl-1-methoxy-[N-(3-carboxy)phenylmethyl-N-isopropyl]aminocarbonyl-1-methoxy-5,6,7,8,12,12b-hexahydro-[9H]-4,8-methano benzofuro[3,2-e]pyrrolo[2,3-g]isoquinoline hydrochloride | Me | H | OMe | —O— | pyrrole with R₇, R₈, NH |
| 105 | [8R-(4bS*,8α,8aβ,12bβ)]-11-Methoxycarbonyl-7,10-dimethyl-1-methoxy-5,6,7,8,9,12b-hexahydro-4,8-methanobenzofuro[3,2-e]thieno[2,3-g]isoquinoline hydrochloride | Me | H | OMe | —O— | thiophene with R₇, R₈, S |

| Ex. | R₆ | R₇ | R₈ | $[\alpha]_D^{20}$ C = 0.1, MeOH | MP (° C.) | m/z | NMR |
|---|---|---|---|---|---|---|---|
| 1 | CON(i-Pr)CH₂Ph | Me | H | −330.1 | 304 dec. | 511(M+); 363; 336; 148; 91 | (CDCl3); 8.46(s br, 1H); 7.31–7.14(m, 5H); 6.69(d, 1H); 6.62(d, 1H); 5.42(s, 1H); 4.66(d, 1H); 4.52(d, 1H); 4.41(dq, 1H); 3.80(s, 3H); 3.25(dd, 1H); 3.07(d, 1H); 2.61–2.47(m, 3H); 2.47(s, 3H); 2.35(dd, 1H); 2.31(ddd, 1H); 2.05–1.89(m, 2H); 1.96(s, 3H); 1.84(dd, 1H); 1.20(d, 3H); 1.16(d, 3H). [free base] |

CHEMICAL TABLE-continued

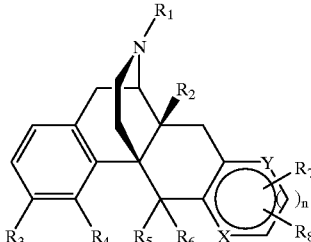

| No. | | | | | | | NMR |
|---|---|---|---|---|---|---|---|
| 2 | CSNEt$_2$ | Me | H | -313.0 | >250 | 451 (M+); 436; 379; | (CDCl3): 8.60(s br, 1H); 6.70(d, 1H); 6.61 (d, 1H); 5.49(s, 1H); 4.00(m br, 2H); 3.80(s, 3H); 3.79(m br, 2H); 3.24(s br, 1H); 3.08(d, 1H); 2.59–2.42(m, 2H); 2.45(s, 3H); 2.39–2.27(m, 2H); 2.00(ddd, 1H); 1.97–1.77(m, 2H); 1.78(s, 3H); 1.24(t, 6H). |
| 3 | CONEt$_2$ | Me | H | -151.8 | 217–218 | 407 (M+); 335; 306 | (CDCl3): 8.38(s br, 1H); 6.81(dd, 1H); 6.62 (d, 1H); 6.40(d, 1H); 4.65(d, 1H); 3.60–3.40 (m, 5H); 3.10(m, 1H); 3.00(m, 2H); 2.59–2.32(m, 3H); 2.44(s, 3H); 2.29–2.13(m, 3H); 2.05–1.80(m, 3H); 1.88(s, 3H); 1.15(t, 6H) |
| 4 | CONEt$_2$ | Me | H | -99.1 | 198–200 dec. | 451 (M+); 379; 207 | (DMSO): 11.10(s br, 1H); 10.60(s, 1H); 6.95–6.85(m, 2H); 4.38(d, 1H); 3.85–3.72(m, 2H); 3.75(s, 3H); 3.68(s, 3H); 3.40–3.10(m, 7H); 2.95(m, 1H); 2.79(d, 3H); 2.45–2.30 (m, 2H); 2.20–2.00(m, 2H); 1.88(m, 1H); 1.79(s, 3H); 1.01(t, 6H). |
| 5 | CON(i-Pr)$_2$ | Me | H | -346.5 | 166–168 | 493 (M+); 393; 378; 362 334; 149 | (CDCl3): 8.28(s br, 1H); 6.68(d, 1H); 6.60(d, 1H); 5.46(s, 1H); 3.89–3.79(m, 2H); 3.80(s, 3H); 3.31(d, 1H); 3.29(d, 1H); 3.21(s, 3H); 2.69(d, 1H); 2.57(m, 1H); 2.51(dd, 1H); 2.42(s, 3H); 2.25(m, 1H); 2.08(d, 1H); 1.92(s, 3H); 1.69–1.60(m, 2H); 1.34(d, 3H); 1.31(d, 3H). |
| 6 | COOEt | Me | H | -508.3 | 251 dec. | 408 (M+); 361; | (CDCl3): 8.90(s br, 1H); 6.76(d, 1H); 6.71 (d, 1H); 5.55(s, 1H); 4.30(q, 2H); 3.85(m, 1H); 3.84(s, 3H); 3.50(m br, 1H); 3.30–3.05 (m, 2H); 2.89(s, 3H); 2.88–2.60(m, 2H); 2.55(dd, 1H); 2.11(s, 3H); 2.09(m, 1H); 1.83 (dd, 1H); 1.35(t, 3H). |
| 7 | CONEt$_2$ | Me | H | -333.4 | 269 dec. | 477(M+); 436; 404; 363 | (CDCl3): 8.48(s br, 1H); 6.66(d, 1H); 6.57(d, 1H); 5.90–5.76(m, 1H); 5.46(s, 1H); 5.28–5.18(m, 2H); 4.76(s br, 1H); 3.80(s, 3H); 3.60–3.35(m, 4H); 3.19–3.06(m, 4H); 2.75(dd, 1H); 2.58(m, 1H); 2.48(d, 1H); 2.35–2.25(m, 3H); 1.90(s, 3H); 1.12(t, 6H). |
| 8 | CONEt$_2$ | Me | H | +10.7 | 105–106 | 513(M+); 439, 413; 207 | (CDCl3): 7.20(dd, 2H); 7.00(s br, 1H); 6.97(d, 1H); 6.93(dd, 1H); 6.76(d, 1H); 6.60(d, 2H); 4.01(d, 1H); 3.58(s, 3H); 3.43(q, 4H); 3.10–3.02(m, 2H); 2.97(dd, 1H); 2.52–2.35(m, 3H); 2.43(s, 3H); 2.25(d br, 1H); 2.19(s br, 1H); 2.13(m, 1H); 1.88(s, 3H); 1.85(m, 1H); 1.77(ddd, 1H); 1.14(t, 6H). |
| 9 | CONEt$_2$ | Me | H | -181.5 | 191–192 | 421(M+); 363; 349; 290 | (CDCl3): 8.27(s br, 1H); 7.04(d, 2H); 6.81(d, 1H); 6.69(dd, 1H); 3.73(s, 3H); 2.62–2.42(m, 4H); 3.39(d, 1H); 3.10(m, 1H); 3.08(d, 1H); 2.85(dd, 1H); 2.66(d, 1H); 2.50(m, 1H); 2.48 (s, 3H); 2.39(dd, 1H); 2.32–2.25(m, 1H); 2.20 (ddd, 1H); 2.10(dd, 1H); 1.97(ddd, 1H); 1.90 (s, 3H); 1.60(d br, 1H); 1.18(t, 6H). |
| 10 | COOEt | CF$_3$ | H | -456.9 | 174 | 462(M+); 415; 372 | (CDCl3): 3.25(9.40(s br, 1H); 6.69(d, 1H); 6.66(d, 1H); 5.40(s, 1H); 4.34(q, 2H); 3.81(s, 3H); dd, 1H); 3.06(d, 1H); 2.73(m, 1H); 2.60–2.42(m, 3H); 2.44(s, 3H); 2.31(ddd, 1H); 2.05–1.86(m, 3H); 1.35(t, 3H) |
| 11 | COOEt | i-Pr | H | -409.7 | 221–223 dec. | 436(M+) | (CDCl3): 8.88(s br, 1H); 6.70(d, 1H); 6.62 (d, 1H); 5.40(s, 1H); 4.32–4.22(m, 2H); 3.81(s, 3H); 3.61(dq, 1H); 3.22(dd, 1H); 3.06(m, 1H); 2.63–2.41(m, 5H); 2.41(s, 3H); 2.31(ddd, 1H); 2.02–1.87(m, 3H); 1.34(t, 3H); 1.19(d, 3H); 1.17(d, 3H). |

CHEMICAL TABLE-continued

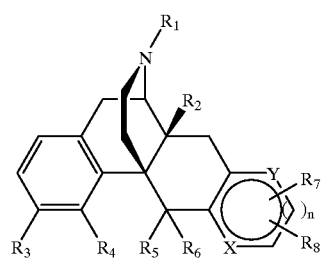

| # | R | R2 | ... | [α] | mp | MS | NMR |
|---|---|---|---|---|---|---|---|
| 12 | CONEt$_2$ | Me | H | −466.9 | 213 | 421(M+); 348; 322 | (CDCl3): 8.40(s br, 2H); 6.70(d, 1H); 6.60 (d, 1H); 5.41(s, 1H); 3.80(s, 3H); 3.52–3.40(m, 5H); 3.09(dd, 1H); 2.85(m, 2H); 2.80(d, 1H); 2.41–2.30(m, 2H); 1.96–1.70(m, 3H); 1.39(s, 3H); 1.18(t, 6H); |
| 13 | COPh | Me | H | −622.2 | 184–187 dec | 440(M+); 382; 241; 105 | (CDCl3): 8.91(s br, 1H); 7.62(d, 2H); 7.51 (dd, 1H); 7.43(dd, 2H); 6.69(d, 1H); 6.62 (d, 1H); 5.45(s, 1H); 3.80(s, 3H); 3.27(dd, 1H); 3.07(d, 1H); 2.62–2.38(m, 4H); 2.45 (s, 3H); 2.32(ddd, 1H); 2.02(ddd, 1H); 1.92 (ddd, 1H); 1.88(s, 3H); 1.85(dd, 1H). |
| 14 | COOH | Me | H | −599.0 | 205–208 | 380(M+); 336 | (CDCl3+TFA): 9.60(s br, 1H); 6.81(d, 1H); 6.79(d, 1H); 5.60(s, 1H); 4.19(s br, 1H); 3.85(s, 3H); 3.55(d br, 1H); 3.18(m, 2H); 3.02–2.80(m, 5H); 2.58(dd, 1H); 2.48 (ddd, 1H); 2.19(ddd, 1H); 2.15(s, 3H); 1.85 (dd, 1H) |
| 15 | CONEt$_2$ | Me | H | −411.9 | 228–229 | 525(M+); 434; 361 | (CDCl3): 8.40(s br, 1H); 7.32–7.18(m, 5H); 6.68(d, 1H); 6.60(d, 1H); 5.46(s, 1H); 3.52–3.40(m, 4H); 3.38(dd, 1H); 3.01(d, 1H); 2.87–2.69(m, 5H); 2.59–2.45(m, 2H); 2.40–2.30(m, 2H); 2.00(ddd, 1H); 1.90 (ddd, 1H); 1.89(s, 3H); 1.82(dd, 1H); 1.15 (t, 6H). |
| 16 | CONEt$_2$ | Me | H | −294.8 | 195–197 | 449(M+); 434; 375; 361 | (CDCl3): 8.40(s br, 1H); 6.63(d, 1H); 6.58 (d, 1H); 5.44(s, 1H); 3.80(s, 3H); 3.55–3.38 (m, 4H); 3.36(dd, 1H); 2.98(d, 1H); 2.67 (ddd, 1H); 2.60(q, 2H); 2.56–2.43(m, 2H); 2.36(dd, 1H); 2.25(ddd, 1H); 1.98(ddd, 1H); 1.97–1.85(m, 1H); 1.89(s, 3H); 1.81 (dd, 1H); 1.15(t, 3H). |
| 17 | COMe | Me | H | −615.0 | 115–140 | 378(M+) | (CDCl3): 9.07(s br, 2H); 6.70(d, 1H); 6.60(d, 1H); 5.40 (s, 1H); 3.80(s, 3H); 3.25(dd, 1H); 3.06(d, 2H); 2.60–2.40(m, 4H); 2.45(s, 3H); 2.40(s, 3H); 2.32(ddd, 1H); 2.15(s, 3H); 2.00(ddd, 1H); 1.91(ddd, 1H); 1.83(dd, 1H) |
| 18 | CO(i-Bu) | Me | H | −497.1 | 221–225 | 420(M+) | CDCl3(free base): 9.10(s br, 1H); 6.659d, 1H); 6.60(d, 1H); 5.41(s, 1H); 3.79(s, 3H); 3.24(dd, 1H); 3.06(d, 1H); 2.60–2.37(m, 4H); 2.55(dd, 2H); 2.44(s, 3H); 2.31(ddd, 1H); 2.22(dq, 1H); 2.14(s, 3H); 1.99(ddd, 1H); 1.90(ddd, 1H); 1.82(dd, 1H); 0.98(d, 3H); 0.97(d, 3H). |
| 19 | CONEt$_2$ | Me | H | −475.2 | 257 dec. | 511(M+); 438; 347; 91 | CDCl3: 8.36(s br, 1H); 7.40–7.22(m, 5H); 6.68(d, 1H); 6.62(d, 1H); 5.43(s, 1H); 3.80(s, 3H); 3.71(q, 2H); 3.55–3.35(m, 5H); 3.25(dd, 1H); 3.09(d, 1H); 2.61–2.49(m, 2H); 2.38(ddd, 1H); 2.30(dd, 1H); 1.99(ddd, 1H); 1.90–1.85(m, 1H); 1.88(s, 3H); 1.79(dd, 1H); 1.11(t, 6H). |
| 20 | CONEt$_2$ | Me | H | −373.7 | 160–162 | 463(M+); 448; 375 | CDCl3: 836(s br, 1H); 6.66(d, 1H); 6.54(d, 1H); 5.43(s, 1H); 3.80(s, 3H); 3.59(dd, 1H); 3.55–3.38(m, 4H); 2.95(d, 1H); 2.89(ddd, 1H); 2.71(dq, 1H); 2.56(dd, 1H); 2.45(m, 1H); 2.34(dd, 1H); 2.21(ddd, 1H); 1.95–1.88(m, 2H); 1.89(s, 3H); 1.80(dd, 1H); 1.17–1.10(m, 12H). |
| 21 | CONEt$_2$ | Me | H | −373.4 | 229 dec. | 463(M+); 434; 361; 210; 58 | CDCl3(free base): 8.42(s br, 1H); 6.68(d, 1H); 6.59(d, 1H); 5.45(s, 1H); 3.79(s, 3H); 3.56–3.39(m, 4H); 3.31(dd, 1H); 2.99(d, 1H); 2.63(dd, 1H); 2.56–2.41(m, 4H); 2.35(dd, 1H); 2.29(ddd, 1H); 1.98(ddd, 1H); 1.90(m, 1H); 1.90(s, 3H); 1.81(dd, 1H); 1.59–1.47(m, 2H); |
| 22 | CON(i-Pr)$_2$ | Me | H | −312.8 | 215 dec. | 477(M+); 376; 350; 100 | CDCl3(free base): 8.29(s br, 1H); 6.66(d, 1H); 6.59(d, 1H); 5.41(s, 1H); 4.10–3.99(m, 2H); 3.88–3.78(m, 2H); 3.21(dd, 1H); 3.04(d, 1H); 2.59–2.42(m, 3H); 2.43(s, 3H); 2.39–2.25(m, 2H); 1.98(ddd, 1H); 1.89(m, 1H); 1.89(s, 3H); 1.81(dd, 1H); 1.38–1.31(m, 15H). |

CHEMICAL TABLE-continued

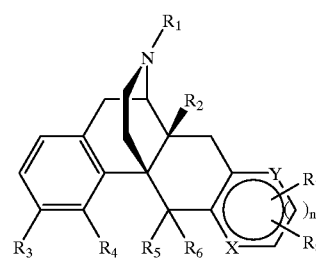

| # | R | | | | mp | MS | NMR |
|---|---|---|---|---|---|---|---|
| 23 | CON(i-Pr)$_2$ | Me | H | −299.1 | 220–225 | 491(M+); 449; 391; 364; 347; 321 | CDCl3(free base): 8.27(s br, 1H); 6.66(d, 1H); 6.58(d, 1H); 5.49(s, 1H); 4.52(dq, 1H); 3.80(dq, 2H); 3.22(dd, 1H); 3.02(d, 1H); 2.59–2.41(m, 3H); 2.42(s, 3H); 2.32(dd, 1H); 2.30(ddd, 1H); 1.98(ddd, 1H); 1.91–1.85(m, 1H); 1.87(s, 3H); 1.83(dd, 1H); 1.35(d, 6H); |
| 24 | CON(i-Pr)$_2$ | CF$_3$ | H | −300.6 | 219–221 dec. | 517(M+); 416; 388; 200; | CDCl3: 9.00(s br, 1H); 6.69(d, 1H); 6.62(d, 1H); 5.39(s, 1H); 3.79(s, 3H); 3.69–3.55(m br, 2H); 3.23(dd, 1H); 3.04(d, 1H); 2.52–2.45(m, 4H); 2.43(s, 3H); 2.30(ddd, 1H); 2.00–1.90(m, 2H); 1.88(ddd, 1H); 1.30(m br, 12H). |
| 25 | CO-i-Bu | Me | H | −463.3 | 198–201 | 462(M+); 421 | CDCl3(free base): 9.12(s br, 1H); 6.68(d, 1H); 6.61(d, 1H); 5.84(ddt, 1H); 5.42(s, 1H); 5.52(d, 1H); 5.18(d, 1H); 4.74(s br, 1H); 3.80(s, 3H); 3.20–3.08(m, 4H); 2.76(dd, 1H); 2.61–2.47(m, 4H); 2.34–2.19(m, 4H); 2.17(s, 3H); 1.79–1.69(m, 1H); 0.96(d, 6H). |
| 26 | CO-i-Bu | Me | H | −478.3 | 245–250 | 448(M+); 407 | CDCl3(base): 9.30(s br, 1H); 6.66(d, 1H); 6.56(d, 1H); 5.84(ddt, 1H); 5.46(s, 1H); 5.22(d, 1H); 5.19(d, 1H); 4.08(s br, 1H); 3.17(d, 2H); 3.14(d, 1H); 3.10(d, 1H); 2.73(dd, 1H); 2.61(m, 1H); 2.58 and 2.54(ABX, 2H); 2.49(d, 1H); 2.37–2.27(m, 2H); 2.30(d, 1H). |
| 27 | CO-i-Bu | Me | H | −471.1 | 259–262 dec. | 476(M+); 435 | CDCl3(base): 8.12(s br, 1H); 6.66(d, 1H); 6.58(d, 1H); 5.84(ddt, 1H); 5.54(s, 1H); 5.22(d, 1H); 5.19(d, 1H); 4.47(s br, 1H); 4.11–3.96(m, 2H); 3.16(d, 2H); 3.15(d, 1H); 3.10(d, 1H); 2.75(dd, 1H); 2.62–2.50(m, 3H); 2.50(d, 1H); 2.29(d, 1H); 2.29–2.20(m, 3H); |
| 28 | CON(iPr)$_2$ | Me | H | −378.0 | 214–244 | 461(M+); 418; 361; 334 | CDCl3(base): 8.27(s br, 1H); 6.86(d, 1H); 6.60(d, 1H); 5.39(s, 1H); 3.87–3.72(m, 2H); 3.22(dd, 1H); 3.06(d, 1H); 2.59–2.48(m, 5H); 2.42(s, 3H); 2.39–2.28(m, 2H); 1.99(ddd, 1H); 1.88(s, 3H); 1.88(m, 1H); 1.80(dd, 1H); 1.31(d, 6H); 1.29(d, 6H); 1.11(t, 3H). |
| 29 | 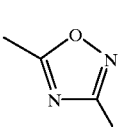 | Me | H | −627.5 | 169–171 | 418(M+) | CDCl3: 8.91(s br, 1H); 6.68(d, 1H); 6.64(d, 1H); 5.48(s, 1H); 3.79(s, 3H); 3.28(dd, 1H); 3.08(d, 1H); 2.60–2.28(m, 5H); 2.46(s, 3H); 2.39(s, 3H); 2.01(s, 3H); 2.01(ddd, 1H); 1.92(ddd, 1H); 1.88(dd, 1H). |
| 30 | CON(i-Pr)$_2$ | Me | H | −436.0 | >300 | 527(M+); 427; 400; 100 | CDCl3(free base): 8.30(s br, 1H); 7.20(d, 1H); 6.44(d, 1H); 5.40(s, 1H); 4.81(s br, 1H); 3.90–3.80(m, 2H); 3.11(d, 1H); 3.01(d, 1H); 2.68(dd, 1H); 2.50(m, 1H); 2.43(s, 3H); 2.39–2.19(m, 4H); 1.91(s, 3H); 1.69(dd, 1H); 1.33(d, 12H). |
| 31 | COOEt | CH$_3$ COOEt | H | −393 | 212–216 | 480(M+); 451; 407; 393; 281; 200 | CDCl3(free base): 9.03(s br, 1H); 6.66(d, 1H); 6.61(d, 1H); 5.45(s, 1H); 4.28(q, 2H); 4.08(q, 2H); 3.80(s, 3H); 3.73(d, 1H); 3.61(d, 1H); 3.22(dd, 1H); 3.04(d, 1H); 2.60–2.42(m, 3H); 2.42(s, 3H); 2.40(dd, 1H); 2.31(ddd, 1H); 1.99(dd, 1H); 1.89(ddd, 1H); |
| 32 | CO-t-Bu | Me | H | −453.7 | 249–252 dec. | 420(M+); 405; 363; 320; 57 | CDCl3(free base): 8.77(s br, 1H); 6.66(d, 1H); 6.62(d, 1H); 5.45(s, 1H); 3.80(s, 3H); 3.25(dd, 1H); 3.06(d, 1H); 2.60–2.40(m, 4H); 2.44(s, 3H); 2.31(ddd, 1H); 2.17(s, 3H); 2.00(ddd, 1H); 1.91(ddd, 1H); 1.82(dd, 1H); 1.32(s, 9H). |
| 33 | CON(i-Pr)$_2$ | Me | H | −499.0 | 280–283 | 511(M+) 411; 384; 100 | CDCl3: 8.34(s br, 1H); 7.20(d, 1H); 6.45(d, 1H); 5.40(s, 1H); 3.88–3.75(m, 2H); 3.30(dd, 1H); 2.97(d, 1H); 2.60–2.43(m, 3H); 2.45(s, 3H); 2.35(dd, 1H); 2.25(ddd, 1H); 1.98(ddd, 1H); 1.89(s, 3H); 1.87(ddd, 1H); 1.78(dd, 1H); 1.31(d, 6H); 1.29(d, 6H). |
| 34 | CO-i-Pr | Me | H | −495.6 | 267–269 | 406(M+); 391; 207; 200 | CDCl3(free base): 9.18(s br, 1H); 6.68(d, 1H); 6.61(d, 1H); 5.41(s, 1H); 3.98(s, 3H); 3.25(dd, 1H); 3.21–3.11(m, 1H); 3.06(d, 1H); 2.60–2.39(m, 4H); 2.44(s, 3H); 2.31(dd, 1H); 2.18(s, 3H); 1.99(ddd, 1H); 1.91(ddd, 1H); 1.83(dd, 1H); 1.16(d, 3H); 1.11(d, 3H). |

CHEMICAL TABLE-continued

| # | R1 | R2 | R3 | [α] | mp | MS | NMR |
|---|---|---|---|---|---|---|---|
| 35 | CO-i-Bu | Me | H | −693 | 300–303 | 468(M+); 411; 283; 57 | CDCl3(free base): 9.12(s br, 1H); 7.10(d, 1H); 6.48(d, 1H); 5.39(s, 1H); 3.32(dd, 1H); 2.98(d, 1H); 2.59 and 2.54(ABX, 2H); 2.59–2.37(m, 4H); 2.45(s, 3H); 2.23(ddd, 1H); 2.22(m, 1H); 2.16(s, 3H); 1.99(ddd, 1H); 1.89(ddd, 1H); 1.78(dd, 1H); 0.99(d, 3H); 0.98(d, 3H). |
| 36 | CON(i-Pr)$_2$ | Me | H | −226 | 222–225 | 419(M+); 376; 319; 292; 100 | CDCl3: 8.00(s br, 1H); 7.22(m, 1H); 7.10(m, 3H); 3.90–3.81(m, 2H); 3.48(d, 1H); 3.11(d, 1H); 3.09(dd, 1H); 2.89(dd, 1H); 2.61(d, 1H); 2.46(ddd, 1H); 2.45(s, 3H); 2.35(dd, 1H); 2.27(m, 1H); 2.15(ddd, 1H); 2.05(m, 2H); 1.94(ddd, 1H); 1.84(s, 3H); |
| 37 | COO-i-Pr | Me | H | −449 | 225–227 dec. | 422(M+); 379; 361; 200 | CDCl3(free base): 8.90(s br, 1H); 6.65(d, 1H); 6.00(d, 1H); 5.41(s, 1H); 5.11(m, 1H); 3.79(s, 3H); 3.23(dd, 1H); 3.04(d, 1H); 2.59–2.43(m, 3H); 2.43(s, 3H); 2.40(dd, 1H); 2.30(ddd, 1H); 2.12(s, 3H); 1.99(ddd, 1H); 1.90(ddd, 1H); 1.82(dd, 1H); 1.31(d, 3H); 1.29(d, 3H). |
| 38 | COO-t-Bu | Me | H | −487 | 257–260 dec. | 436(M+); 379; 363; 243; 200 | CDCl3(free base): 8.81(s br, 1H); 6.69(d, 1H); 6.61(d, 1H); 5.37(s, 1H); 3.80(s, 3H); 3.24(dd, 1H); 3.05(d, 1H); 2.59–2.44(m, 3H); 2.44(s, 3H); 2.40(dd, 1H); 2.31(ddd, 1H); 2.11(s, 3H); 1.99(ddd, 1H); 1.90(ddd, 1H); 1.82(dd, 1H); 1.53(s, 9H). |
| 39 | COOMe | Me | H | −474.4 | 232–235 dec. | 394(M+); 361; 200 | CDCl3(free base): 8.90(s br, 1H); 6.68(d, 1H); 6.62(d, 1H); 5.46(s, 1H); 3.80(s, 3H); 3.79(s, 3H); 3.24(dd, 1H); 3.06(d, 1H); 2.59–2.45(m, 3H); 2.45(s, 3H); 2.40(dd, 1H); 2.31(ddd, 1H); 2.12(s, 3H); 1.99(ddd, 1H); 1.90(ddd, 1H); 1.82(d, 1H). |
| 40 | COO-n-Pr | Me | H | −462.2 | 230–232 dec. | 422(M+); 405; 361; 285; 200 | CDCl3(free base): 8.90(s br, 1H); 6.66(d, 1H); 6.60(d, 1H); 5.40(s, 1H); 4.20(t, 2H); 3.80(s, 3H); 3.24(dd, 1H); 3.05(d, 1H); 2.59–2.43(m, 3H); 2.43(s, 3H); 2.40(dd, 1H); 2.31(ddd, 1H); 2.13(s, 3H); 1.99(ddd, 1H); 1.90(ddd, 1H); 1.82(d, 1H); 1.79–1.66(m, 2H); 1.00(t, 3H). |
| 41 | CO-i-Bu | Me | H | −449.7 | 291–294 dec. | 432(M+) | CDCl3(free base): 9.25(s br, 1H); 7.61(d, 1H); 6.74(d, 1H); 5.55(s, 1H); 3.27(dd, 1H); 3.10(d, 1H); 2.61–2.51(m, 4H); 2.52(s, 3H); 2.46–2.40(m, 1H); 2.44(s, 3H); 2.30–2.13(m, 3H); 2.17(s, 3H); 2.02(ddd, 1H); 1.89(ddd, 1H); 1.79(dd, 1H); 0.98(d, 6H). |
| 42 | COCOOEt | Me | H | −365.0 | 190 dec. | 436(M+); 407; 362; 191 | CDCl3(free base): 9.50(s br, 1H); 6.78(d, 1H); 6.70(d, 1H); 5.52(s, 1H); 4.28(q, 2H); 3.80(s, 3H); 3.54(m, 1H); 3.28(m, 1H); 3.10–2.98(m, 3H); 2.88(s, 3H); 2.68(m, 2H); 2.60(s, 3H); 2.10–2.00(m, 3H); 1.40(t, 3H). |
| 43 | CO-i-Bu | Me | H | −195 | 215 dec. | 422(M+); 379; 285; 192 | CDCl3(free base): 8.70(s br, 1H); 6.68(d, 1H); 6.61(d, 1H); 5.93(s, 1H); 4.62(d, 1H); 3.80(s, 3H); 3.06(m, 1H); 3.00(d, 1H); 2.88(dd, 1H); 2.60–2.40(m, 5H); 2.41(s, 3H); 2.25–2.10(m, 4H); 2.13(s, 3H); 1.96(ddd, 1H); 1.81(ddd, 1H); 0.96(d, 3H); 0.94(d, 3H). |
| 44 | CO-i-Bu | Me | H | −177.3 | 208 dec. | 464(M+); 254 | CDCl3(free base): 8.80(s br, 1H); 6.62(d, 1H); 6.58(d, 1H); 5.98(s, 1H); 5.83(ddt, 1H); 5.20(d, 1H); 5.15(d, 1H); 4.45(s br, 1H); 4.41(d, 1H); 3.79(s, 3H); 3.15–3.00(m, 5H); 2.85(d, 1H); 2.60–2.50(m, 3H); 2.48–2.35(m, 2H); 2.22–2.00(m, 3H); 2.10(s, 3H); 1.68(m, 1H); 0.96(d, 3H); 0.94(d, 3H) |
| 45 | CO-i-Bu | Me | H | −476.6 | 205–209 | 446(M+) | CDCl3(free base): 9.10(s br, 1H); 6.67(d, 1H); 6.60(d, 1H); 5.89(ddt, 1H); 5.41(s, 1H); 5.22(d, 1H); 5.15(d, 1H); 3.80(s, 3H); 3.36(dd, 1H); 3.27–3.12(m, 2H); 3.00(d, 1H); 2.65(dd, 1H); 2.56–2.35(m, 2H); 2.35–2.11(m, 3H); 2.15(s, 3H); 1.98(ddd, 1H); 1.90(ddd, 1H); 1.80(dd, 1H); 0.98(d, 6H) |
| 46 | CON(i-Pr)$_2$ | Me | H | −93.2 | 190–195 | 507(M+); 464; 407; 380; 365; | CDCl3: 8.20(s br, 1H); 6.95(d, 1H); 6.75(d, 1H); 4.00(d, 1H); 3.91–3.82(m, 2H); 3.70(s, 3H); 3.29(m, 1H); 3.10(dd, 1H); 3.00(d, 1H); 2.68(dd, 1H); 2.55(d, 1H); 2.49(s, 3H); 2.43–2.11(m, 4H); 2.29(s, 3H); 1.92(ddd, 1H); 1.88(s, 3H); 1.74(d br, 1H); 1.32(d, 12H). |

CHEMICAL TABLE-continued

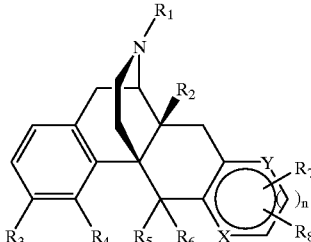

| | | | | | | | |
|---|---|---|---|---|---|---|---|
| 47 | CO-i-Bu | Me | H | 185.8 | 216–220 | 462 (M+); 378; 252 | CDCl3(free base): 8.86(s br, 1H); 6.60(m, 2H); 5.82(d, 1H); 5.82(ddt, 1H); 5.72(d, 1H); 5.20(d, 1H); 5.06(d, 1H); 4.41(s br, 1H); 3.83(d, 1H); 3.18–3.09(m, 3H); 3.05–2.92(m, 2H); 2.81(d, 1H); 2.60–2.30(m, 6H); 2.28–2.02(m, 2H); 2.11(s, 3H); 1.51(m, 1H); 0.96(d, 6H). |
| 48 | CO-3-pentyl | Me | H | −598.7 | 260–262 dec. | 434 (M+); 417; 235 | CDCl3(free base): 9.16(s br, 1H); 6.69(d, 1H); 6.60(d, 1H); 5.42(s, 1H); 3.80(s, 3H); 3.25(dd, 1H); 3.08(d, 1H); 2.93(m, 1H); 2.60–2.40(m, 4H); 2.43(s, 3H); 2.31(ddd, 1H); 2.19(s, 3H); 1.99(ddd, 1H); 1.90(ddd, 1H); 1.83(dd, 1H); 1.74(dq, 2H); 1.50(dq, 2H). |
| 49 | CO-i-Pr | Me | H | −569.5 | 240–243 | 420 (M+); 405; 377 | CDCl3(free base): 6.68(d, 1H); 6.61(d, 1H); 5.50(s, 1H); 3.91(s, 3H); 3.81(s, 3H); 3.28–3.18(m, 2H); 3.06(d, 1H); 2.60–2.42(m, 3H); 2.43(s, 3H); 2.41(dd, 1H); 2.32(ddd, 1H); 2.13(s, 3H); 1.99(ddd, 1H); 1.92(ddd, 1H); 1.82(dd, 1H); 1.15(d, 3H); 1.12(d, 3H). |
| 50 | CON(i-Pr)$_2$ | Me | H | −353.7 | 209–210 | 479 (M+); 379; 352 | CDCl3(free base): 8.28(s br, 1H); 6.67(d, 1H); 6.59(d, 1H); 5.43(s, 1H); 5.58(s br, 1H); 3.90–3.79(m, 2H); 3.79(s, 3H); 3.20(d, 1H); 2.94(d, 1H); 2.72(dd, 1H); 2.47(d, 1H); 2.45(m, 2H); 2.41(s, 3H); 2.41(d, 1H); 2.30(m, 1H); 1.91(s, 3H); 1.72(m, 1H); 1.32(d, 6H); 1.30(d, 6H). |
| 51 | Me | Me | H | −305.5 | 132–136 | 350 (M+) | CDCl3: 7.70(s br, 1H); 6.67(d, 1H); 6.60(d, 1H); 5.49(s, 1H); 3.80(s, 3H); 3.40(m, 1H); 3.05(d, 1H); 2.70–2.55(m, 3H); 2.50(s, 3H); 2.40(m, 1H); 2.34(m, 1H); 2.10(s, 3H); 2.02(m, 1H); 1.89(ddd, 1H); 1.79(dd, 1H); 1.78(s, 3H). |
| 52 | CON(i-Pr)$_2$ | Me | H | −182.2 | 204–207 | 513 (M+); 470; 433. | CDCl3: 8.55(s br, 1H); 6.97(d, 1H); 6.22(d, 1H); 4.68(d, 1H); 3.89–3.80(m, 2H); 3.06(d, 1H); 2.81(d, 1H); 2.71(dd, 1H); 2.50–2.30(m, 3H); 2.38(s, 3H); 2.20–1.95(m, 5H); 1.81(s, 3H); 1.72(ddd, 1H); 1.25(d, 12H). |
| 53 | 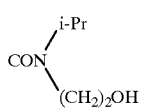 | Me | H | −383.9 | 247–250 | 470 (M+); 361; 200; 91 | CDCl3(free base): 8.90(s br, 1H); 7.41–7.31(m, 5H); 6.66(d, 1H); 6.61(d, 1H); 5.40(s, 1H); 5.26(s, 2H); 3.80(s, 3H); 3.22(dd, 1H); 3.05(d, 1H); 2.59–2.45(m, 3H); 2.42(s, 3H); 2.40(dd, 1H); 2.30(ddd, 1H); 2.14(s, 3H); 1.99(ddd, 1H); 1.89(ddd, 1H); 1.81(dd, 1H). |
| 54 | CON(i-Pr)$_2$ | Me | H | −402.8 | 219–220 | 489 (M+); 388; 361; 347 | CDCl3: 8.22(s br, 1H); 6.68(d, 1H); 6.60(d, 1H); 5.89(ddt, 1H); 5.43(s, 1H); 5.24(d, 1H); 5.15(d, 1H); 3.85–3.76(m, 2H); 3.80(s, 3H); 3.34(dd, 1H); 3.25–3.12(m, 2H); 2.99(d, 1H); 2.62(ddd, 1H); 2.50(d, 1H); 2.49(m, 1H); 2.34(dd, 1H); 2.29(ddd, 1H); 1.98(ddd, 1H); 1.89(m, 1H); 1.89(s, 3H); 1.80(dd, 1H); 1.33(d, 6H); 1.31(d, 6H). |
| 55 | COO-i-Bu | Me | H | −153 | 265–266 | 438 (M+); 301 | CDCl3(free base): 8.48(s br, 1H); 6.61(d, 1H); 6.59(d, 1H); 5.71(s br, 1H); 4.61(d, 1H); 3.99(d, 2H); 3.79(s, 3H); 3.04(dd, 1H); 3.00(d, 1H); 2.39(dd, 1H); 2.41–2.36(m, 3H); 2.41(s, 3H); 2.25–2.10(m, 3H); 2.11(s, 3H); 2.05–1.90(m, 2H); 1.81(ddd, 1H); 0.92(d, 6H). |
| 56 | CON(i-Pr)$_2$ | Me | H | −388 | 254–156 | 493 (M+); 462; 361 | CDCl3: 8.25(s br, 1H); 6.68(d, 1H); 6.60(d, 1H); 5.45(s, 1H); 3.86–3.75(m, 2H); 3.79(s, 3H); 3.59(m, 2H); 3.24(dd, 1H); 2.95(d, 1H); 2.80(m, 1H); 2.73–2.61(m, 4H); 2.50(m, 1H); 2.45–2.31(m, 2H); 1.95–1.88(m, 2H); 1.88(s, 3H); 1.80(dd, 1H); 1.31(d, 6H); 1.29(d, 6H). |
| 57 | CONH$_2$ | Me | H | −463.2 | 279–281 | 379 (M+); 362; 347 | CDCl3(free base): 9.42(s br, 1H); 6.62(d, 1H); 6.58(d, 1H); 5.63(s br, 2H); 5.48(s, 1H); 3.80(s, 3H); 3.24(dd, 1H); 3.06(d, 1H); 2.59–2.42(m, 3H); 2.42(s, 3H); 2.40(dd, 1H); 2.31(ddd, 1H); 2.11(s, 3H); 1.99(ddd, 1H); 1.91(ddd, 1H); 1.84(dd, 1H). |
| 58 | 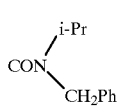 | Me | H | −316.3 | 219–221 | 527 (M+); 252; 148; 106; 91 | CDCl3(free base): 8.50(s br, 1H); 7.28–7.15(m, 5H); 6.66(d, 1H); 6.60(d, 1H); 5.41(s, 1H); 4.63(d, 1H); 4.51(d, 1H); 4.41(dq, 1H); 3.78(s, 3H); 3.20(d, 1H); 2.94(d, 1H); 2.73(dd, 1H); 2.50–2.44(m, 2H); 2.41(s, 3H); 2.37–2.27(m, 3H); 1.98(s, 3H); 1.77–1.67(m, 2H); 1.16(d, 6H). |

CHEMICAL TABLE-continued

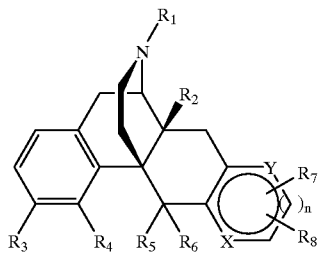

| # | R | | | | | | | |
|---|---|---|---|---|---|---|---|---|
| 59 | CON(i-Pr)(CH₂)₂OH | Me | H | −161.3 | 238–242 | 467 (M+); 381; 336; 85; 72 | CDCl3(free base): 8.77(s br, 1H); 6.61(d, 1H); 6.59(d, 1H); 5.93(s br, 1H); 4.61(d, 1H); 4.30(m, 2H); 3.80(s, 3H); 3.05(m, 1H); 2.97–2.89(m, 4H); 2.83(dq, 1H); 2.52–2.38(m, 3H); 2.41(s, 3H); 2.23–2.13(m, 3H); 2.11(s, 3H); 1.95(m, 1H); 1.81(ddd, 1H); 1.01(d, 6H). | | |
| 60 | COOCH₂Ph | Me | H | −399.2 | 206–210 | 470 (M+); 361; 200; 91 | CDCl3(free base): 8.90(s br, 1H); 7.41–7.31(m, 5H); 6.66(d, 1H); 6.61(d, 1H); 5.40(s, 1H); 5.26(s, 2H); 3.80(s, 3H); 3.22(dd,, 1H); 3.05(d, 1H); 2.59–2.45(m, 3H); 2.42(s, 3H); 2.40(dd, 1H); 2.30(ddd, 1H); 2.14(s, 3H); 1.99(ddd, 1H); 1.89(ddd, 1H); 1.81(dd, 1H). | | |
| 61 | COO-i-Bu | Me | H | −428.78 | 285–288 | 448 (M+); 391; 373 | CDCl3(free base): 9.00(s br, 1H); 7.63(d, 1H); 6.75(d, 1H); 5.58(s, 1H); 4.04(ABX, 2H); 3.27(dd, 1H); 3.10(d, 1H); 2.60–2.51(m, 3H); 2.53(s, 3H); 2.45(s, 3H); 2.43(dd, 1H); 2.25(ddd, 1H); 2.14(s, 3H); 2.09–1.95(m, 2H); 1.89(ddd, 1H); 1.79(dd, 1H); 1.00(d, 6H). | | |
| 62 | CON(i-Pr)₂ | Me | H | −384.1 | 279–280 | 477 (M+); 377; 349 | CDCl3(free base): 6.68(d, 1H); 6.59(d, 1H); 5.50(s, 1H); 3.80(s, 3H); 3.70(s br, 2H); 3.60(s, 3H); 3.20(dd, 1H); 3.03(d, 1H); 2.59–2.42(m, 3H); 2.42(s, 3H); 2.36–2.27(m, 2H); 1.99(ddd, 1H); 1.90(ddd, 1H); 1.82(dd, 1H); 1.80(s, 3H); 1.32(s br, 12H). | | |
| 63 | COOCH(CHMe₂)₂ | Me | H | −150.3 | 218–220 | 478 (M+); 461; 379; 363. | CDCl3(free base): 8.90(s br, 1H); 5.68(d, 1H); 6.61(d, 1H); 5.45(s, 1H); 4.78(dd, 1H); 3.80(s, 3H); 3.25(dd, 1H); 3.07(d, 1H); 2.59–2.42(m, 3H); 3.42(s, 3H); 2.41(dd, 1H); 2.31(ddd, 1H); 2.15(s, 3H); 2.03–1.91(m, 4H); 1.85(dd, 1H); 0.91(d, 6H); 0.89(d, 1H). | | |
| 64 | COO-i-Bu | Me | H | −665.2 | 211–214 | 484 (M+); 411; 299; 158. | CDCl3: 8.84(s br, 1H); 7.20(d, 1H); 6.48(d, 1H); 5.40(s, 1H); 4.04(ABX, 2H); 3.32(dd, 1H); 2.98(d, 1H); 2.61–2.48(m, 3H); 2.48(s, 3H); 2.41(dd, 1H); 2.25(ddd, 1H); 2.13(s, 3H); 2.09–1.91(m, 2H); 1.89(ddd, 1H); 1.79(dd, 1H); 0.99(d, 6H). | | |
| 65 | COO-i-Bu | Me | H | −260.2 | 231–236 | 392 (M+); 208; 184; 173. | CDCl3(free base): 8.50(s br, 1H); 7.20(m, 1H); 7.09(m, 3H); 3.99(d, 2H); 3.42(d, 1H); 3.12(d, 1H); 3.11(dd, 1H); 2.39(dd, 1H); 2.63(d, 1H); 2.51–2.46(m, 1H); 2.46(s, 3H); 2.41(dd, 1H); 2.29(m, 1H); 2.15(ddd, 1H); 2.11–1.91(m, 3H); 2.08(s, 3H); 1.59(m, 1H); 0.98(d, 6H). | | |
| 66 | CON(i-Pr)₂ | Me | H | −345.5 | 117–121 | 535 (M+); 462; 361 | CDCl3: 8.20(s br, 1H); 6.67(d, 1H); 6.60(d, 1H); 5.42(s, 1H); 4.20(q, 2H); 3.81(m, 2H); 3.80(s, 3H); 3.42(d, 1H0; 3.37(dd, 1H); 3.31(d, 1H); 2.94(d, 1H); 2.71(dd, 1H); 2.67–2.58(m, 2H); 2.40(ddd, 1H); 2.34(dd, 1H); 2.06(ddd, 1H); 1.89(s, 3H); 1.88(m, 1H); 1.79(dd, 1H); 1.34(d, 6H); 1.32(d, 6H); 1.29(t, 3H). | | |
| 67 | CON(i-Pr)₂ | Me | H | −321.9 | 240–244 | 507 (M+) | (DMSO): 6.90(d, 1H); 6.87(d, 1H); 5.79(s, 1H); 4.28(m, 1H); 4.12–3.98(m, 2H); 3.79(s, 3H); 3.79–3.65(m, 2H); 3.57(m, 1H); 3.40–3.22(m, 2H); 3.05(m, 1H); 2.90(m, 1H); 2.60(m, 1H); 2.39(ddd, 1H); 2.20(m, 1H); 1.88–1.80(m, 1H); 1.85(s, 3H); 1.23(m, 12H). | | |
| 68 | CONMe₂ | Me | H | −363.3 | 228–229 dec. | 407 (M+); | CDCl3: 8.58(s br, 1H); 6.66(d, 1H); 6.61(d, 1H); 5.44(s, 1H); 3.80(s, 3H); 3.22(dd, 1H); 3.06(d, 1H); 3.02(s, 6H); 2.59–2.44(m, 3H); 2.44(s, 3H); 2.34(dd, 1H); 2.31(ddd, 1H); 1.99(ddd, 1H); 1.91(m, 1H); 1.90(ddd, 1H); 1.82(dd, 1H). | | |
| 69 | COO-i-Bu | Me | H | 184.5 | 297–298 dec. | 422 (M+); 363; 349; 214 | CDCl3(base): 8.48(s br, 1H); 7.01(d, 1H); 6.72(d, 1H); 6.65(dd, 1H); 3.99(d, 2H); 3.71(s, 3H); 3.35(d, 1H); 3.10(dd, 1H); 3.08(d, 1H); 2.81(dd, 1H); 2.62(d, 1H); 2.49(m, 1H); 2.44(s, 3H); 2.41(dd, 1H); 2.25(m, 1H); 2.18–1.90(m, 4H); 2.09(s, 3H); 1.59(m, 1H); 0.92(d, 6H). | | |

CHEMICAL TABLE-continued

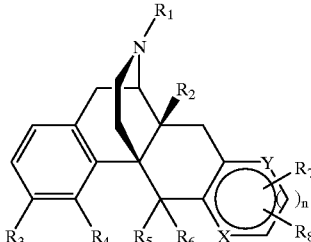

| # | R | R' | R'' | value | mp | MS | NMR |
|---|---|---|---|---|---|---|---|
| 70 | CON(i-Pr)$_2$ | Me | H | −335.5 | 172–177 | 449 (M+); 406; 349; 322. | CDCl3: 8.30(s br, 1H); 6.70(d, 1H); 6.61(d, 1H); 5.40(s, 1H); 3.89–3.79(m, 1H); 3.80(s, 3H); 2.61–2.49(m, 1H); 3.09(dd, 1H); 2.85(m, 1H); 2.82(d, 1H); 2.50–2.42(m, 1H); 2.35(dd, 1H); 1.95–1.70(m, 6H); 1.88(s, 3H); 1.32(d, 6H); 1.30(d, 6H). |
| 71 | COOH | CH$_3$ COOH | H | −357.7 | 235 dec. | 425 (MH+); 407. [FAB POS] | DMSO(disodium salt): 10.93(s br, 1H); 6.66(d, 1H); 6.59(d, 1H); 5.36(s, 1H); 3.58(s, 3H); 3.45(m, 1H); 3.15(m, 3H); 2.93(d, 1H); 2.49–2.39(m, 1H); 2.38–2.24(m, 2H); 2.30(s, 3H); 2.12(ddd, 1H); 1.90(ddd, 1H); 1.70–1.59(m, 2H). |
| 72 | CON(i-Pr)$_2$ | Me | H | −357.7 | 282–286 | 506 (M+); 462; 369; 361. | CDCl3: 8.30(s br, 1H); 6.74(d, 1H); 6.68(d, 1H); 5.50(s, 1H); 3.90–3.80(m, 2H); 3.84(s, 3H); 3.32(d, 1H); 3.31(m, 1H); 3.12(d, 1H); 2.95(d, 1H); 2.77(dd, 1H); 2.70–2.60(m, 1H); 2.60–2.50(m, 2H); 2.40(dd, 1H); 2.00–1.92(m, 2H); 1.92(s, 3H); 1.85(dd, 1H); 1.37(d, 6H); 1.35(d, 6H). |
| 73 | CSN(i-Pr)$_2$ | Me | H | −364.9 | 296 dec. | 479 (M+); 436; 379; 33 | CDCl3: 8.20(s br, 1H); 6.73(d, 1H); 6.68(d, 1H); 5.50(s, 1H); 4.30(m, 2H); 3.88(m, 1H); 3.80(s, 3H); 3.24(m, 2H); 3.08(m, 2H); 2.92–2.70(m, 1H); 2.88(s, 3H); 2.50(m, 1H); 2.44(dd, 1H); 2.08(dd, 1H); 1.81(dd, 1H); 1.81(s, 3H); 1.45(s br, 12H). |
| 74 | COO-i-Bu | Me | H | −465.4 | 270–272 dec. | 494 (M+); 450; 437; 393; 295. | DMSO: 12.10(s br, 1H); 6.79(d, 1H); 6.71(d, 1H); 5.72(s, 1H); 5.08(d, 1H); 4.92(d, 1H); 3.92(ABX, 2H); 3.85(m, 1H); 3.70(s, 3H); 3.21(d, 1H); 3.08–2.80(m, 3H); 2.78(s, 3H); 2.62(m, 1H); 2.45(dd, 1H); 2.23(ddd, 1H); 2.09(s, 3H); 2.00–1.88(m, 2H); 1.69(dd, 1H); 0.91(d, 6H). |
| 75 | CON(i-Pr)$_2$ | Me | H | −221.4 | 180–184 | 435 (M+); 335; 308; 232. | CDCl3: 8.04(s br, 1H); 7.20(m, 1H); 7.05(m, 3H); 4.58(s br, 1H); 3.95–3.81(m, 2H); 3.23(d, 1H); 3.15(d, 1H); 3.00(dd, 1H); 2.93–2.88(m, 2H); 2.45–2.30(m, 3H); 2.39(s, 3H); 2.23–2.11(m, 3H); 1.80(s, 3H); 1.31(d, 12H). |
| 76 | COO-i-Bu | Me | H | — | 230–235 | 408 (M+); 182 | CDCl3: 8.53(s br, 1H); 7.18(m, 1H); 7.09(m, 3H); 4.55(s br, 1H); 3.99(d, 2H); 3.26(d, 1H); 3.19(d, 1H); 3.06–2.91(m, 3H); 2.41(s, 3H); 2.40(m, 3H); 2.23–2.10(m, 2H); 2.08(s, 3H); 2.05–1.91(m, 1H); 1.79(m, 1H); 0.97(d, 6H). |
| 77 | CON(i-Pr)$_2$ | Me | H | −174.5 | 190–193 | 461 (M+); 361; 334. | CDCl3(base): 8.05(s br, 1H); 7.20(m, 1H); 7.05(m, 3H); 5.86(ddt, 1H); 5.21(d, 1H); 5.15(d, 1H); 4.57(s br, 1H); 3.93–3.83(m, 2H); 3.25–3.10(m, 4H); 3.08–2.89(m, 3H); 2.51(m, 1H); 2.41(m, 2H); 2.32(d, 1H); 2.21–2.09(m, 3H); 1.82(s, 3H); 1.30(d, 12H). |
| 78 | CON(i-Pr)$_2$ | Me | H | −308.3 | 206–216 dec. | 519 (M+); 419; 392; 377; 351. | CDCl3(base): 8.30(s br, 1H); 6.64(d, 1H); 6.58(d, 1H); 5.83(ddt, 1H); 5.42(s, 1H); 5.21(d, 1H); 5.18(d, 1H); 4.80(s br, 1H); 4.10–3.95(m, 2H); 3.90–3.80(m, 2H); 3.18–3.08(m, 4H); 2.75(dd, 1H); 2.62–2.51(m, 1H); 2.45(d, 1H); 2.32–2.20(m, 3H); 1.90(s, 3H); 1.78–1.68(m, 1H); 1.31(d, 6H); 1.30(t, 3H); 1.29(d, 6H). |
| 79 | CON(i-Pr)$_2$ | Me | H | −377.5 | 248–250 dec. | 521 (M+) | DMSO: 6.8–6.6(m, 2H); 5.6(s, 1H); 4.65(q, 2H); 4.1–3.6(m, 6H); 3.4–2.8(m, 4H); 2.5–1.7(m, 10H); 1.3 (m, 12H) |
| 80 | 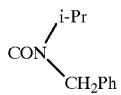 | Me | H | −346.1 | 204–207 dec. | 569 (M+) 525, 134, 91. | DMSO(base, 373K): 7.25(m, 5H); 6.6(m, 2H); 5.55 (s, 1H); 4.8–4.4(m, 4H); 3.7(s, 3H); 3.4(m, 1H); 3.1 (d, 1H); 2.8–2.3(m, 9H); 2.1(m, 1H); 1.7–1.9(m, 5H); 1.1(m, 6H). |
| 81 | COO-i-Bu | Me | H | −415.2 | 196–200 | 493 (M+) | CDCl3(base): 8.8(bs, 1H); 6.6(q, 2H); 5.75–5.9(m, 1H); 5.4(s, 1H); 5.3–5.1(m, 2H); 4.7(bs, 1H); 4.0(m, 4H); 3.2–3.0(m, 4H0; 2.8–2.65(dd, 1H); 2.6–2.45(m, 2H); 2.35–1.9(m, 7H); 1.75(m, 1H); 1.3(m, 3H); 1.0 (m, 6H) |
| 82 | COOMe | Me | H | −490.1 | 140 dec. | 409.1 (M+) | CDCl3(base): 6.6(q, 2H); 5.5(s, 1H); 3.95(s, 3H); 3.8(s, 6H); 3.25–2.85(m, 4H); 2.6–2.2(m, 8H); 2.1(s, 3H). |

CHEMICAL TABLE-continued

| | | | | | | | |
|---|---|---|---|---|---|---|---|
| 83 | CON(i-Pr)$_2$ | Me | H | −455.4 | 187–190 | 492.2 (M+) | |
| 84 | CON(i-Pr)$_2$ | Me | H | −198.9 | 178–182 | 536.1 (M+) | |
| 85 | COO-i-Bu | Me | H | −424.5 | 174–175 dec. | 523.3 (M+) | CDCl3(base): 6.62–6.65(m, 2H); 5.10–5.42(m, 3H); 4.20–4.35(m, 2H); 3.9–4.0(m, 2H); 3.75(s, 3H); 3.22 (m, 1H); 3.05(d, 1H); 2.6–2.2(m, 8H); 2.15(s, 3H); 2.0–1.7(m, 8H). |
| 86 | COO-i-Bu | Me | H | −395.3 | 245–246 dec. | 583.9 (M+) | CDCl3(base): 7.3–7.1(m, 5H); 6.7–6.55(m, 2H); 6.1 (bs, 1H); 5.55(s, 1H); 5.1(s, 2H); 4.6(m, 1H); 4.3–4.15(m, 1H); 4.0–3.9(m, 2H); 3.8(s, 3H); 3.25(m, 1H); 3.1(d, 1H); 2.6–2.2(m, 8H); 2.1(s, 3H); 2.0–1.7(m, 4H); 0.9(d, 6H) |
| 87 | CON(i-Pr)$_2$ | Me | H | −406.3 | 124–126 dec. | 549.9 (M+) | CDCl3(base): 6.6(m, 2H); 5.4(s, 1H); 5.0(d, 1H); 4.8–4.7(m, 1H); 4.2(m, 2H); 3.8(s, 3H); 3.2(m, 1H); 3.0(d, 1H); 2.6–2.2(m, 8H); 2.0–1.7(m, 9H); 1.5–1.1 (m, 15H). |
| 88 | CO-i-Bu | Me | H | −660 | 138–140 dec. | 434.9 (M+) | CDCl3(base): 6.6(m, 2H); 5.5(s, 1H); 3.95(s, 3H); 3.85(s, 3H); 3.25(m, 1H); 3.1(d, 1H); 2.6–2.2(m, H); 2.15(s, 3H); 2.15–1.75(m, 3H); 0.95(m, 6H). |
| 89 | PO(OEt)$_2$ | Me | H | −359.5 | 131–134 dec. | | CDCl3(base): 8.6(bs, 1H); 6.6(q, 2H); 5.4(s, 1H); 4.2–3.0(m, 4H); 3.8(s, 3H); 3.25–3.0(m, 2H); 2.6–2.2 (m, 5H); 2.4(s, 3H); 2.0(s, 3H); 1.95–1.75(m, 3H); 1.3(m,6H). |
| 90 | CON(i-Pr)(CH$_2$CF$_3$) | Me | H | −338.2 | >260 dec. | 503.8 (M+) | CDCl3(base): 8.56(bs, 1H); 6.65(m, 2H); 5.4(s, 1H); 4.4–3.8(m, 3H); 3.8(s, 3H); 3.2(m, 1H); 3.1(d, 1H); 2.6–2.3(m, 8H); 2.0–1.75(m, 6H); 1.2(m, 6H); |
| 91 | COO-i-Bu | Me | H | −507.6 | >250 dec. | 423.1 (M+) | CDCl3(base): 8.9(bs, 1H); 6.6(m, 2H); 5.4(s, 1H); 4.0(m, 2H); 3.8(s, 3H); 3.5(m, 1H); 3.1(dd, 1H); 2.8 (m, 3H); 2.4(m, 2H); 2.15(s, 3H); 2.0–1.7(m, 4H); 1.0(d, 6H). |
| 92 | COO-i-Bu | Me | H | −457.44 | −250 dec. | 422.8 (M+) | CDCl3(base): 9.1(bs, 1H); 6.6–6.5(dd, 2H); 5.4(s, 1H); 4.0(m, 2H); 3.2(m, 1H); 3.0(d, 1H); 2.6–2.3(m, 5H); 2.4(s, 3H); 2.1(s, 3H); 2.0–1.7(m, 5H); 1.0(d, 6H) |
| 93 | COO-i-Bu | Me | H | 432.9 | >270 dec. | 523.0 (M+) | DMSO(base): 11.5(s, 1H); 6.5(s, 2H); 5.9–5.7(m, 1H); 5.3–5.1(m, 3H); 4.7–4.5(m, 1H); 4.1–3.9(m, 4H); 3.2–2.9(m, 5H); 2.8–2.55(m, 1H); 2.4–1.9(m, 6H); 2.05(s, 3H); 1.5(d, 1H); 0.9(d, 6H). |
| 94 | COO-i-Bu | Me | H | −479.4 | 235–237 dec. | 501.9 (M+) | CDCl3(base): 6.6(m, 2H); 5.75(m, 1H); 5.55(s, 1); 5.1–4.9(m, 2H); 4.0(d, 2H); 3.8(s, 3H); 3.25(m, 1H); 3.1–1.0(d, 1H); 2.8(d, 3H); 2.6–2.25(m, 5H); 2.45(s, 3H); 2.15(s, 3H); 2.05–1.75(m, 4H); 0.95(d, 6H). |
| 95 | COO-i-Bu | Me | H | −577.6 | 240–242 dec. | 522.0 (M+) | CDCl3(base): 6.6(m, 2H); 5.7(d, 1H); 5.5(s, 1H); 4.95(d, 1H); 3.9(m, 2H); 3.8(s, 3H); 3.2(m, 2H); 3.15(s, 3H); 3.0(s, 3H); 2.6–2.2(m, 5H); 2.4(s, 3H); 2.1(s, 3H); 2.1–1.8(m, 4H); 0.9(d, 6H). |
| 96 | CON-pyrrolidinyl | Me | H | −412.5 | 244–246 dec. | 434.0 (M+) | CDCl3(base): 8.7(bs, 1H); 6.6(m, 2H); 5.4(s, 1H); 3.8(s, 3H); 3.5(m, 4H); 3.3–3.0(m, 2H); 2.6–2.2(m, 5H); 2.4(s, 3H); 1.9(s, 3H); 1.9–1.7(m, 7H). |
| 97 | CON-piperidinyl | Me | H | −386.1 | 262 dec. | 447.8 (M+) | CDCl3(base): 8.7(bs, 1H); 6.6(m, 2H); 5.4(s, 1H); 3,8(s, 3H); 3.5(m, 4H); 3.3–3.0(m, 2H); 2.6–2.2(m, 5H); 2.4(s, 3H); 1.9(s, 3H); 1.9–1.7(m, 9H). |

CHEMICAL TABLE-continued
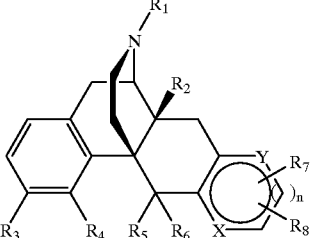
| | | | | | | | |
|---|---|---|---|---|---|---|---|
| 98 |  | Me | H | −376.2 | 258–260 dec. | 449.9 (M+) | CDCl3(base): 8.7(bs, 1H); 6.6(m, 2H); 5.4(s, 1H); 3.8(s, 3H); 3.7(s, 3H); 3.6–3.5(m, 5H); 3.25–3.0(m, 2H); 2.4(s, 3H); 2.6–2.2(m, 5H); 1.9(s, 3H); 2.0–1.8 (m, 3H). |
| 99 | 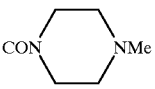 | Me | H | −424.8 | 255 . 258 dec. | 462.9 (M+) | CDCl3(base): 8.7(bs, 1H); 6.6(m, 2H); 5.4(s, 1H); 3.8(s, 3H); 3.6(m, 4H); 3.2(m, 1H); 3.05(d, 1H); 2.6–2.2(m, 15); 2.0–1.8(m, 6H). |
| 100 | 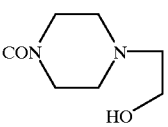 | Me | H | −301.0 | 106–107 dec. | | CDCl3(base): 8.7(bs, 1H); 6.6(m, 2H); 5.4(s, 1H); 3.8(s, 3H); 3.6(m, 6H); 3.2(m, 1H); 3.0(d, 1H); 2.6–2.2(m, 12H); 2.0–1.7(m, 9H). |
| 101 | 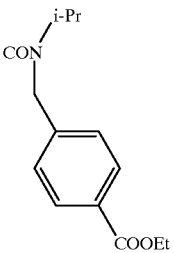 | Me | H | −303.1 | 249–253 | 583.9 (M+) | CDCl3(base): 8.5(s, 1H); 7.9(d, 2H); 7.3(m, 2H), 6.65(m, 2H); 5.45(s, 1H); 4.6(q, 2H); 4.5(m, 3H); 3.8(s, 3H); 3.25(m, 1H); 3.1(d, 1H); 2.55–2.2(m, 8H); 2.05–1.8(m, 6H); 1.4(t, 3H); 1.15(m, 6H). |
| 102 | 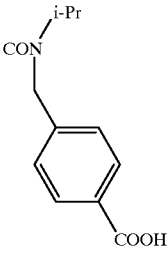 | Me | H | −368.3 | 215–220 | 555.8 (M+) | CDCl3: 11.2(s, 1H); 7.85(d, 2H); 7.3(m, 2H); 6.6 (q, 2H); 5.4(s, 1H); 4.6(s, 2H); 4.25(m, 1H); 3.65 (s, 3H); 3.3(m, 1H); 3.1(d, 1H); 2.5–1.6(m, 14H), 0.9(m, 6H). |
| 103 | 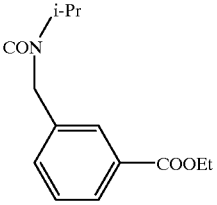 | Me | H | −303.5 | 200–204 | 583.9 (M+) | CDCl3(base): 8.5(s, 1H); 7.9(m, 2H); 7.5–7.3(m, 2H); 6.6(m, 2H); 5.4(s, 1H); 4.7–4.3(m, 5H); 3.8(s, 3H); 3.3(m, 1H); 3.1(d, 1H); 2.6–2.2(m, 8H); 2.0–1.7(m, 6H); 1.4(t, 3H); 1.15(m, 6H) |
| 104 | 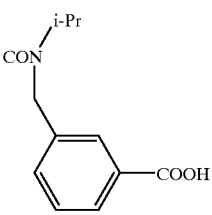 | Me | H | −318.8 | 242–246 | 556 (M+) | CDCl3(base): 11.3(s, 1H); 7.8–7.75(m, 2H); 7.5–7.3 (m, 2H); 6.75–6.65(q, 2H); 5.5(s, 1H); 4.6(s, 2H); 4.3(m, 1H); 3.9(m, 1H); 3.7(s, 3H); 3.5–2.7(m, 9H); 2.3(m, 2H); 2.0–1.8(m, 4H); 1.65(m, 1H); 1.1 (m, 6H). |

CHEMICAL TABLE-continued

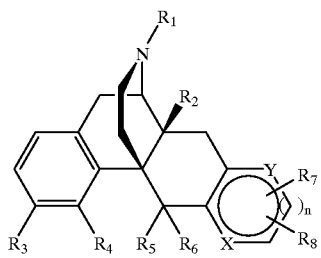

| | | | | | | | |
|---|---|---|---|---|---|---|---|
| 105 | COOMe | | Me | H | −425.9 | 150 dec. | 412 (MH+) | CDCl3(base): 6.68(d, 1H); 6.63(d, 1H); 5.52(s, 1H); 3.82(s, 3H); 3.81(s, 3H); 3.25(dd, 1H); 3.08 (d, 1H); 2.61–2.42(m, 4H): 2.44(s, 3H); 2.33(ddd, 1H); 2.31(s, 3H); 2.01(ddd, 1H); 1.93(ddd, 1H); 1.82(dd, 1H). |

What is claimed is:

1. A compound, or a solvate or salt thereof, of formula (I):

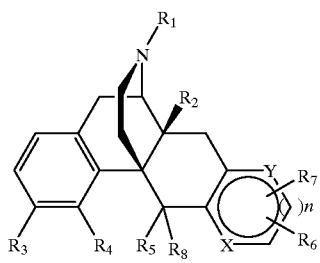

(I)

in which,

- $R_1$ is hydrogen, linear or branched $C_{1-6}$ alkyl, $C_{3-7}$ cycloalkyl, $C_{4-6}$ cycloalkylalkyl, each of the latter three groups being optionally substituted by a hydroxy group when $C_{\geq 2}$, $C_{3-5}$ alkenyl, aryl, aralkyl or furan-2 or 3-yl alkyl or $(CH_2)_m COR$ wherein m is 0 to 5 and R represents linear or branched $C_{1-6}$ alkyl, hydroxy, $C_{1-5}$ alkoxy, $OC_{3-6}$ alkenyl or alkylaryl, $NR_{10}R_{11}$ where $R_{10}$ and $R_{11}$ may be the same or different, and each is hydrogen, linear or branched $C_{1-6}$ alkyl, $C_{4-6}$ cycloalkylalkyl, $C_{3-5}$ alkenyl, aryl or aralkyl;
- $R_2$ is hydrogen, hydroxy or $C_{1-5}$ alkoxy, halogen, nitro, $NR_{10a}R_{11}$, or $SR_{10a}$, where $R_{10a}$ is hydrogen, linear or branched $C_{1-6}$ alkyl, $C_{4-6}$ cycloalkylalkyl, $C_{3-5}$ alkenyl, aryl, aralkyl or $COR_1$, and $R_{11}$ has the same meaning described above; $R_3$ is hydrogen, linear or branched $C_{1-6}$ alkyl, hydroxy, $C_{1-5}$ alkoxy, halogen, or $(CH_2)_m COR$ where m and R have the same meaning described above, $SR_{10}$, nitro, $NR_{10}R_{11}$, $NHCOR_{10}$, $NHSO_2R_{10}$, where $R_{10}$ and $R_{11}$ have the same meaning described above;
- $R_4$ and $R_5$, which may be the same or different, are each independently hydrogen, hydroxy, $C_{1-5}$ alkoxy, O-phenyl or together may form an oxy group (—O—); or $R_4$ together with $R_3$ may form a methylenedioxy group (—OCH$_2$[2]O—); $R_6$ is CONH$_2$, CONMe$_2$, CONEt$_2$, CON(i-Pr)$_2$, CON(i-Pr)CH$_2$Ph, CON(i-Pr)(CH$_2$)$_2$OH, CON(CH$_2$CF$_3$)(i-Pr), COOMe, COOEt, COO-n-Pr, COO-i-Pr, COO-i-Bu, COOCH(i-Pr)$_2$, CSNEt$_2$, CSN(i-Pr)$_2$, COOH, COMe, CO-i-Pr, CO-i-Bu, CO-t-Bu, CO-3-pentyl, COPh,

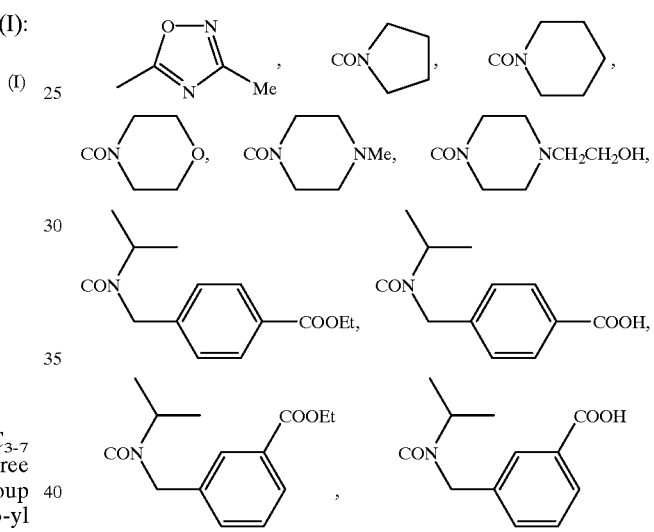

or PO(OEt)$_2$;

- $R_7$ is hydrogen, $C_{1-18}$ alkyl, $C_{2-18}$ alkenyl, halogen, halogen-$C_{1-6}$ alkyl, $(CH_2)_m COR$ where m and R have the same meanings defined above or is a group

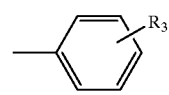

or a five- or six-membered heteroaromatic group, containing up to three heteroatoms selected from O, S and N, and substituted with $R_3$ in which $R_3$ has the same meaning described above;

- $R_8$ is hydrogen or $C_{1-6}$ alkyl;
- n is 0;
- X and Y are independently oxygen, sulphur, CH or a $R_6$- or $R_7$-substituted carbon atom, and NR$_9$, where $R_9$ is hydrogen, linear or branched $C_{1-6}$ alkyl, $C_{3-7}$ cycloalkyl, $C_{4-6}$ cycloalkylalkyl, each of the latter three groups being optionally substituted by a hydroxy group when $C_{\geq 2}$, or may contain a $NR_{10b}R_{11b}$ group where $R_{10b}$ and $R_{11b}$ may be the same or different and each is hydrogen, linear or branched $C_{1-6}$ alkyl, $C_{4-6}$ cycloalkylalkyl, $C_{3-5}$ alkenyl, aryl, aralkyl, $C_{3-5}$ alkenyl, aryl, aralkyl or $(CH_2)_m COR$ wherein m is 0 to 5 and R represents hydroxy, $C_{1-5}$ alkoxy, $OC_{3-6}$ alkenyl or alkylaryl, $NR_{10c}R_{11c}$ where $R_{10c}$ and $R_{11c}$ may be the same or different, are each hydrogen, linear or branched $C_{1-6}$ alkyl, $C_{4-6}$ or cycloalkylalkyl.

2. A compound according to claim 1 in which $R_1$ is hydrogen, methyl, ethyl, propyl, i-propyl, allyl, benzyl, phenyl-ethyl, $CH_2CH_2OH$, $CH_2COOH$, $CH_2COOEt$, $CH_2CONH_2$ or COMe.

3. A compound according to claim 1 in which $R_3$ is hydrogen, hydroxy, ethyl, bromine, hydroxy, methoxy, ethoxy, i-propoxy, COMe or $OCH_2COOH$.

4. A compound according to claim 1 in which $R_4$ and $R_5$ are each hydrogen, hydroxy, acetyloxy, methoxy, O-phenyl, or together form an oxy group, or $R_4$ together with $R_3$ is a methylenedioxy group.

5. A compound according to claim 1 in which n=0, X is NH and Y is CH or a $R_6$- or $R_7$-substituted carbon atom, where $R_6$ is $CONH_2$, $CONMe_2$, $CONEt_2$, $CON(i-Pr)_2$, $CON(i-Pr)CH_2Ph$, $CON(i-Pr)(CH_2)_2OH$, $CON(CH_2CF_3)(i-Pr)$, COOMe, COOEt, COO-n-Pr, COO-i-Pr, COO-i-Bu, or $COOCH(i-Pr)_2$; and $R_7$ is methyl or halogen-$C_{1-2}$alkyl.

6. A pharmaceutical composition comprising a compound according to claim 1 and a pharmaceutically acceptable carrier.

7. A process for the preparation of a compound of formula (I) as defined in claim 1 or a solvate or salt thereof, which comprises condensing a compound of formula (a), where K is H, Br, $COR_7$, =CHOH or =NOH, with a compound of formula (b), where Q is $COR_7$, $CHClR_7$, $COR_7$, SH or $NH_2$, and J is =NNHPh, =O, =$H_2$, or =$CHR_7$, where $R_7$ and $R_6$ are as defined in claim 1

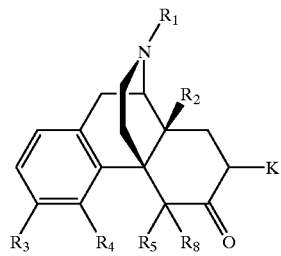
(a)

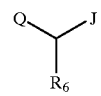
(b)

and optionally thereafter converting the compound of formula (I) to a solvate or salt thereof.

* * * * *